US008031335B2

(12) United States Patent
Wang et al.

(10) Patent No.: US 8,031,335 B2
(45) Date of Patent: Oct. 4, 2011

(54) NON-INVASIVE DISEASE DIAGNOSIS USING LIGHT SCATTERING PROBE

(75) Inventors: Hong Wang, Cupertino, CA (US); Xun Guo, Sacramento, CA (US)

(73) Assignee: Opto Trace Technologies, Inc., Mountain View, CA (US)

( * ) Notice: Subject to any disclaimer, the term of this patent is extended or adjusted under 35 U.S.C. 154(b) by 322 days.

(21) Appl. No.: 12/176,383

(22) Filed: Jul. 20, 2008

(65) Prior Publication Data

US 2009/0086202 A1    Apr. 2, 2009

Related U.S. Application Data

(63) Continuation-in-part of application No. 11/681,157, filed on Mar. 1, 2007, now Pat. No. 7,428,046, which is a continuation of application No. 10/987,842, filed on Nov. 12, 2004, now Pat. No. 7,242,469, which is a continuation-in-part of application No. 10/852,787, filed on May 24, 2004, now Pat. No. 7,384,792.

(60) Provisional application No. 60/473,283, filed on May 27, 2003, provisional application No. 60/473,287, filed on May 27, 2003, provisional application No. 60/520,222, filed on Nov. 17, 2003.

(51) Int. Cl.
*G01J 3/44* (2006.01)

(52) U.S. Cl. ........................................ 356/301

(58) Field of Classification Search ............... 356/301
See application file for complete search history.

(56) References Cited

U.S. PATENT DOCUMENTS

| 4,933,274 | A | 6/1990 | Sanford |
| 5,017,007 | A | 5/1991 | Milne |
| 5,244,788 | A | 9/1993 | Hubscher |
| 5,527,712 | A | 6/1996 | Sheehy |
| 5,864,397 | A * | 1/1999 | Vo-Dinh ................. 356/301 |
| 6,361,861 | B2 | 3/2002 | Gao |
| 6,406,777 | B1 | 6/2002 | Boss |
| 6,614,523 | B1 | 9/2003 | Boss |
| 2002/0123050 | A1 | 9/2002 | Poponin |
| 2003/0059820 | A1 | 3/2003 | Vo-Dinh |
| 2003/0175472 | A1 | 9/2003 | Den |
| 2004/0106203 | A1 | 6/2004 | Stasiak |
| 2005/0070778 | A1 * | 3/2005 | Lackey et al. ............ 600/366 |
| 2005/0136552 | A1 | 6/2005 | Buechler |

* cited by examiner

*Primary Examiner* — Tarifur Chowdhury
*Assistant Examiner* — Abdullahi Nur
(74) *Attorney, Agent, or Firm* — SV Patent Service

(57) ABSTRACT

A method for non-invasive detection of a disease, a status of illicit-drug use, or smoking status includes transferring a body fluid obtained from a patient to a sensor comprising a nano-scale surface structure to allow the body fluid to come in contact with the nano-scale surface structure, illuminating the body fluid and the nano-scale surface structure by a laser beam, scattering the laser beam by the body fluid and the nano-scale surface structure to produce a scattered light, and analyzing the scattered light using a spectral analyzer to diagnose a disease, the status of illicit-drug use, or smoking status in the patient.

36 Claims, 19 Drawing Sheets

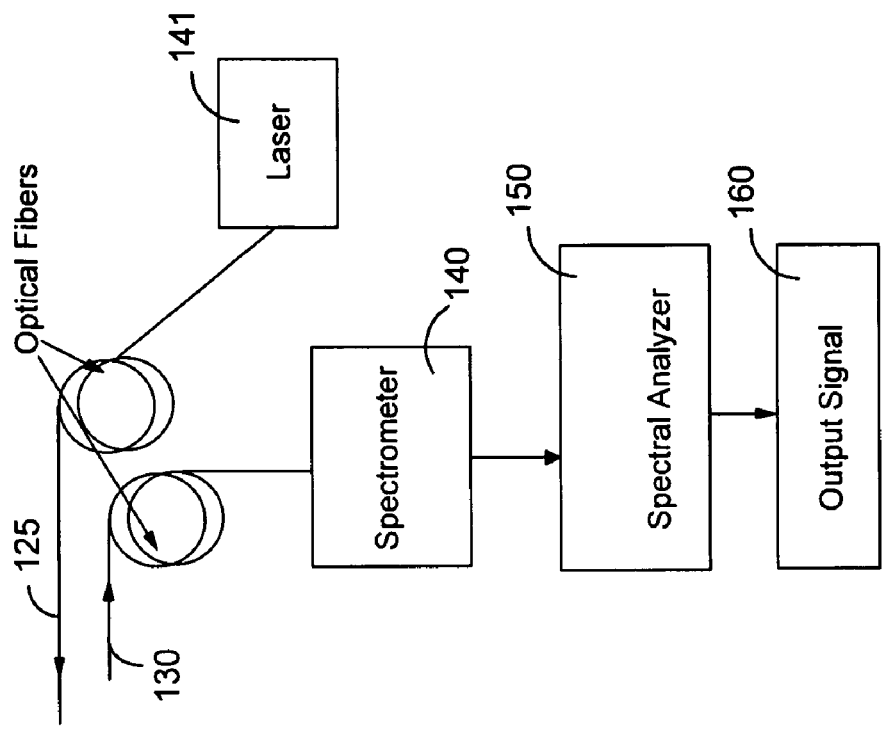
Fig. 1C
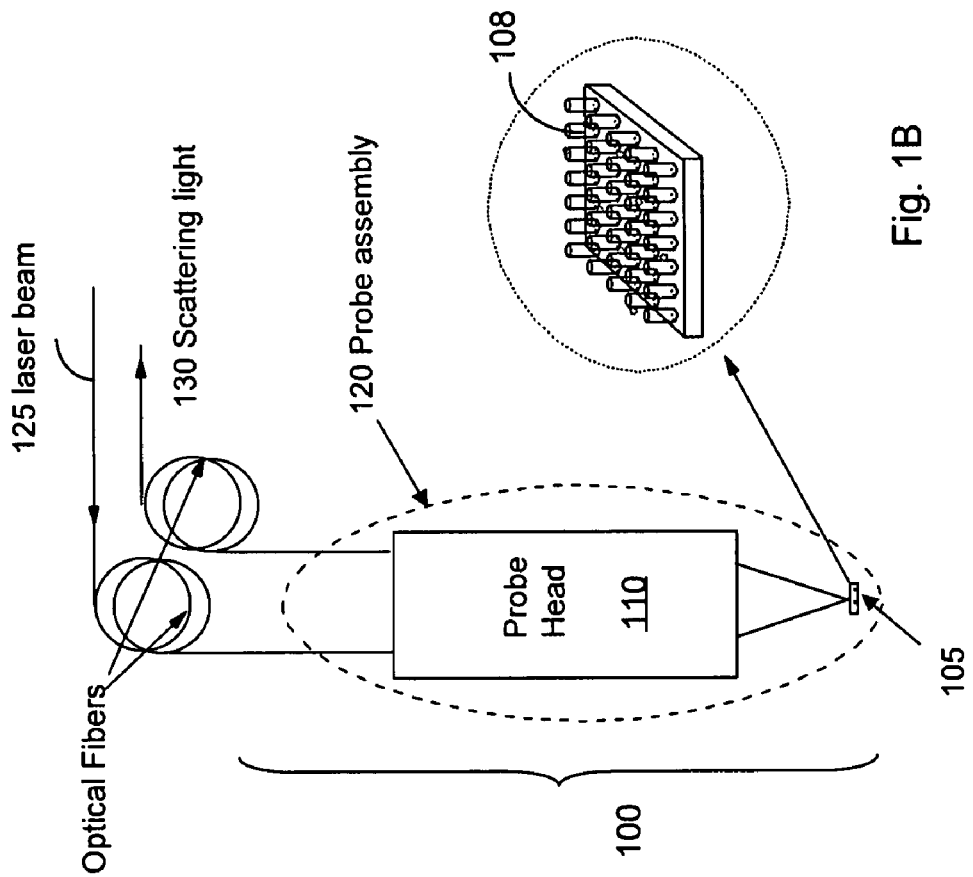
Fig. 1B
Fig. 1A

SECTION A-A

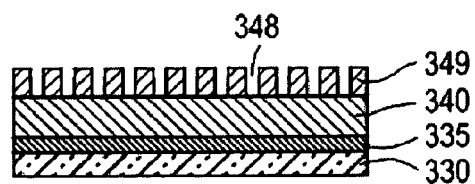
FIG. 16A  FIG. 16D
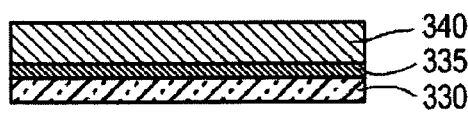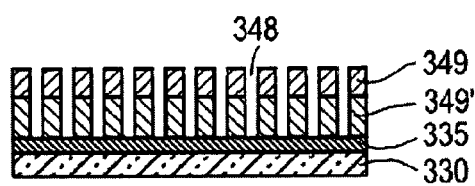
FIG. 16B  FIG. 16G
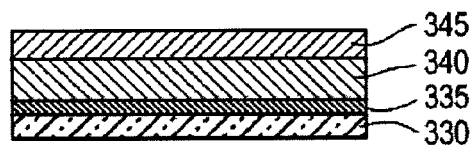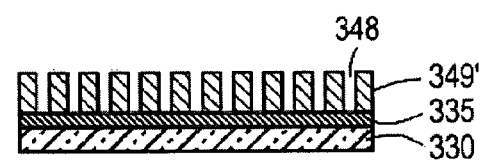
FIG. 16C  FIG. 16H
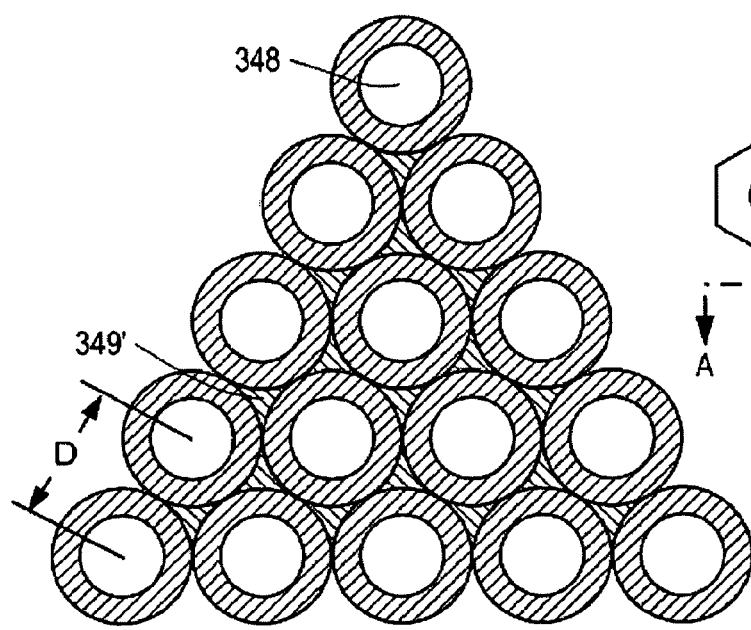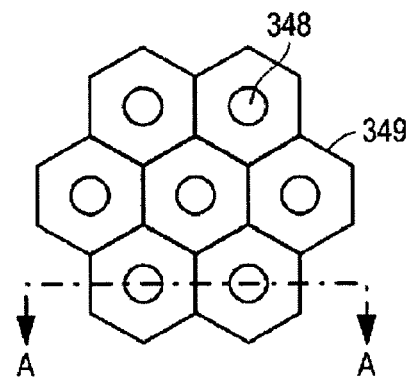
FIG. 16F  FIG. 16E

NON-INVASIVE DISEASE DIAGNOSIS USING LIGHT SCATTERING PROBE

The present application is a Continuation-in-Part (CIP) patent application of commonly assigned U.S. patent application Ser. No. 11/681,157, entitled "Trace chemical optical probe", filed Mar. 1, 2007 now U.S. Pat. No. 7,428,046. U.S. patent application Ser. No. 11/681,157 is a continuation application of commonly assigned U.S. patent application Ser. No. 10/987,842 filed Nov. 12, 2004 (now issued as U.S. Pat. No. 7,242,469), which is a CIP patent application of U.S. patent application Ser. No. 10/852,787 (now issued as U.S. Pat. No. 7,384,792) filed on Mar. 24, 2004. U.S. patent application Ser. No. 10/852,787 claims priority to Provisional Patent Applications 60/473,283 and 60/473,287 filed on May 27, 2003, and Provisional Patent Application 60/520,222 filed on Nov. 17, 2003.

BACKGROUND

This invention relates generally to the methods and systems for detection of very small amount of chemicals (trace chemicals) by employing light scattering probes. More particularly, this invention relates to an improved light scattering probe and a chemical sensor.

Despite the fact Raman detectors have sensitivity down to a level of single molecule detection (SMD), due to several technical difficulties; conventional Raman sensors still have very limited applications. Specifically, one of the major limitations of Raman spectroscopy application is the weak Raman scattering signal for trace chemical detection. There are many efforts in attempt to resolve this problem of low scattering signals in the field of Raman sensing. However, such efforts still have very limited success and have not been able to make Raman detectors available for practical and economical applications that urgently require ultra sensitive chemical trace detections.

Roughened or nano-structured sensing surface is known to generate strong scattering signals. Specifically, the nano-structured materials have found numerous applications in sensing, bioscience, materials science, semiconductor, etc. One of the promising applications of sensing technologies with nano-structured materials is Surface-Enhanced Raman Spectroscopy (SERS) and Surface-Enhanced Resonance Raman Spectroscopy (SERRS). It has been discovered that the Raman scattering signal can be enhanced by $10^4 \sim 10^{14}$ times when molecules are adsorbed on a nano-structured noble metal (such as Ag Au and Cu, but not limited to Ag, Au and Cu) surface compared to normal Raman scattering. Specially, Raman scattering signal gets remarkably enhanced if the surface nanoparticles are isolated. The enhancement is determined by several factors, among them, the dimensions of the nano-particles and the distance among these nanoparticles on the surface are very important. It is found that as the scale of these nanoparticles decreases, the signal enhancement of Raman scattering increases. Further, as the distance between neighboring nanoparticles islands varies, the enhancement effect of Raman scattering also varies. However, the conventional technologies, for example, VLSI lithography technology, are still encountered with technical difficulties to fabricate nano-structure surfaces with reduced dimensions of the nano-particles and reduced distance among these nano-particles on the surface to achieve scattering signal enhancement.

The very limited availability of non-contaminated nano-structured noble metal surface is still a major difficulty faced by those of ordinary skill of the art in applying the technologies of SERS (Surface-Enhanced Raman Scattering) and SERRS (Surface-Enhanced Resonant Raman Scattering) for trace chemical detection. A non-contaminated nano-structured noble metal surface is required to conveniently deploy in the field for molecular adsorption and subsequent measurement. Due to this limit availability, even though the detection of trace chemicals can be achieved a part-per-billion (ppb) level, the techniques of applying SERS and SERRS for detecting trace of explosives and/or other chemical materials still have very limited applications.

The technologies of applying SERS and SERRS for detecting trace chemicals were described in many published papers such as "Probing Single Molecules And Single Nanoparticles by Surface Enhanced Raman Scattering", Shuming Nie and Steven R. Emory, Science, 1997, 275, 1102-1106; "Surface Enhanced Raman Spectroscopy of Individual Rhodamine 6G Molecules on Large Ag Nanocrystals", Amy M Michaels, M. Nirmal, and L. E. Brus. J. Am. Chem. Soc. 1999, 121, 9932-9939; "Single Molecule Detection Using Surface-Enhanced Raman Scattering (SERS)", Katrin Kneipp, Yang Wang, Harald Kneipp, Lev L. Perelman, Irving Itzkan, Physical Review Letter, 78, 1997. 1667-1670; "Nanosphere Lithography: A Versatile Nanofabrication Tool for Studies of Size-Dependent Nanoparticle Optics", Christy L. Haynes and Richard P. Van Duyne, J. Phys. Chem. B 2001, 105, 5599-5611.

However, these publications do not provide an effective method to produce and package the non-contaminated nano-structured noble metal surface to achieve field applications of SERS and SERRS for trace chemical detection. Furthermore, none of these publications provide method to fabricate nano-structured materials with well-controlled nano array that have reduced and optimized dimensions of the nano-particles and reduced and optimized distances among these nano-particles on the surface to achieve scattering signal enhancement.

There are ever increasing demands to take advantage of the greatly improved nano-structured surface now provided by the invention as that disclosed in the co-pending Application so that Raman sensors can be practically implemented to effectively realize these applications that are urgently in demand.

Therefore, a need still exists in the art to provide practical configuration for conveniently implement the Raman sensors in applications to antiterrorism, forensic, medical diagnoses, disease preventions, industrial process monitoring, environmental cleaning up and monitoring, food, and drug quality control, etc.

SUMMARY OF THE INVENTION

In one aspect, the present invention relates to a method for non-invasive detection of a disease, illicit-drug use status, or smoking status. The method includes transferring a body fluid obtained from a patient to a sensor comprising a nano-scale surface structure to allow the body fluid to come in contact with the nano-scale surface structure; illuminating the body fluid and the nano-scale surface structure by a laser beam; scattering the laser beam by the body fluid and the nano-scale surface structure to produce a scattered light; and analyzing the scattered light using a spectral analyzer to detect a disease, the status of illicit-drug use, or smoking status in the patient.

In another aspect, the present invention relates to a method for non-invasive detection of a disease, illicit-drug use status, or smoking status. The method includes transferring a body fluid obtained from a patient to a sensor comprising a nano-scale surface structure to allow the body fluid to come in contact with the nano-scale surface structure; illuminating the body fluid and the nano-scale surface structure by a laser beam; scattering the laser beam by the body fluid and the nano-scale surface structure to produce a scattered light; obtaining a Raman spectrum of the scattered light; and identifying a spectral signature around a predetermined wavelength in the Raman spectrum to detect the disease, the status of illicit-drug use, or smoking status in the patient, wherein the spectral signature includes at least one spectral peak around the predetermined wavelength in the Raman spectrum.

Implementations of the system may include one or more of the following. The body fluid can include blood, saliva, urine, serum, tear, sweat, sperm, and secrete body fluids including stomach fluid (secrete gastric juice), female secret body fluid, etc. The disease can be selected from the group consisting of lung cancer, breast cancer, stomach cancer, liver cirrhosis, a failing kidney, ulcer cancer, ovarian cancer, uterus cancer, cervix cancer, oral cancer, esophageal cancer, thyroid cancer, larynx cancer, leukemia, colon cancer, bladder cancer, prostate cancer, bronchus cancer, HIV, drug addiction, diabetes, and smoking status. The disease can include an illicit use of a drug selected from a group consisting of heroin, methamphetamine, cocaine, caffeine, morphine, codeine, amphetamine, ephedrine, papaverine, narcotine, and MDMA. The body fluid transferred to the sensor can have a volume in a range from about 100 pl to 1 ml. The step of analyzing can include obtaining a Raman spectrum of the scattered light; and analyzing the Raman spectrum to diagnose the disease in the patient. The step of analyzing can include identifying a spectral signature around a predetermined wavelength in the Raman spectrum to diagnose the disease in the patient. The spectral signature can include at least one spectral peak around the predetermined wavelength in the Raman spectrum. The step of analyzing can include determining if a signal-to-noise ratio for the spectral peak in the Raman spectrum is above a pre-determined threshold value; and alerting a possibility of the disease in the patient if the spectral peak is above the pre-determined threshold value. The pre-determined threshold value for the signal-to-noise ratio can be about 3 or higher. The disease can be oral cancer, wherein the body fluid is saliva, wherein the step of analyzing comprises analyzing a spectral signature around $560\,cm^{-1}$ or $1100\,cm^{-1}$ in the Raman spectrum to diagnose oral cancer in the patient. The disease can be breast cancer, wherein the body fluid is saliva, wherein the step of analyzing comprises analyzing a spectral signature around $560\,cm^{-1}$ or $1100\,cm^{-1}$ in the Raman spectrum to diagnose breast cancer in the patient. The disease can be lung cancer, wherein the body fluid is blood serum, wherein the step of analyzing includes analyzing a spectral signature around $745\,cm^{-1}$ in the Raman spectrum to diagnose lung cancer in the patient. The disease can be HIV (virus), wherein the body fluid is saliva, wherein the step of analyzing can include analyzing a spectral signature around $870\,cm^{-1}$ in the Raman spectrum to diagnose HIV in the patient. The body fluid can be saliva, wherein the step of analyzing comprises analyzing a spectral signature around at least one of peaks around $1030\,cm^{-1}$ and $1535\,cm^{-1}$ in the Raman spectrum to detect status of illicit drug use by the patient. The body fluid is saliva, wherein the step of analyzing can include analyzing a spectral signature around $1123\,cm^{-1}$ in the Raman spectrum to detect glucose level of diabetes patient. The body fluid is saliva, wherein the step of analyzing can include analyzing a spectral signature around $1029\,cm^{-1}$ in the Raman spectrum to detect smoking status of the patient. The body fluid is saliva, wherein the step of analyzing can include analyzing a spectral signature around $1130\,cm^{-1}$ in the Raman spectrum to diagnose diabetes in the patient. The algorithm can include a dendrographic algorithm and a Principal Component Analysis.

The method can further include adsorbing molecules in the body fluid by a surface of the nano-scale surface structure, wherein the step of scattering comprises scattering the laser beam by the molecules adsorbed on the surface of the nano-scale surface structure. The nano-scale surface structure can include a conductive material. The conductive material can include a noble metal. The sensor can further include a substrate, and wherein the nano-scale surface structure comprises a plurality of columns over the substrate or a plurality of holes in the substrate. The sensor can further include a conductive layer on the substrate, and wherein the plurality of columns are formed on the conductive layer. The sensor can further include a conductive layer on the substrate, and wherein the plurality of holes are formed at least partially in the conductive layer. Neighboring columns in the plurality of columns or neighboring holes in the plurality of holes can be separated by a distance in the range of 10 nanometers to 1000 nanometers.

Embodiments may include one or more of the following advantages. The disclosed systems and methods provide simple and non-invasive approach to detect a disease in a patient. The disclosed systems are portable and easy to operate, and are thus ideal for being used for early disease prevention, and in-field drug usage screening. The disclosed systems and methods are suitable for early detect and diagnosis. The disclosed systems and methods also have short testing cycle, and can therefore be very helpful for monitoring progresses in the treatment of diseases and drug use. The disclosed systems and methods can detect a wide range of disease such as oral cancer, breast cancer, lung cancer, stomach cancer, liver cirrhosis, a failing kidney, ulcer cancer, ovarian cancer, uterus cancer, cervix cancer, oral cancer, esophageal cancer, thyroid cancer, larynx cancer, leukemia, colon cancer, bladder cancer, prostate cancer, bronchus cancer, diabetes, HIV, smoking status as well as illicit drug use.

The present application describes applications of Raman scattering probe with or without a sensor (e.g. RamanNanoChip™). Since a sensor provides much higher sensitivity in SERS compared with conventional enhance surface, some applications that were not practical before have now become practically achievable. Because the significant improvement in Raman scattering achieved by the sensor broader scopes of applications are now enabled and can be practically implemented as now disclosed in this application.

Furthermore, a wide range of applications that should be achievable with relative low Raman sensitivity detections implementing conventional Raman Scattering were also overlooked and neglected due to low expectation of Raman sensing capabilities. New and improved Raman sensing applications are also disclosed in this invention that do not require high detection sensitivities and do not require surface enhanced Raman sensing devices such as such sensor applications. The embodiments disclosed in this invention thus expand the fields of applications for devices that implement Raman scattering sensing technologies.

In applications of first category, detected trace chemicals are typically in any phase, such as gas, liquid, solid, which gas can be from solid with certain value of vapor pressure. The laser beam doesn't strike on sample under detection, and the scattering light is not collected from sample directly neither, that makes the detection to be "remote and non-invasive". The detected molecules and background materials are adsorbed onto the surface of the sensor. The trapped molecules have much larger scattering cross section than that they are free in gas, liquid or solid. When laser beam strikes on trapped molecules, Raman Scattering occurs and Spectrograph and data analyzer obtains a Raman Spectrum of molecules. Since every chemical has its own special Raman spectrum, then one is able to apply this principal as Raman fingerprint to identify unknown chemicals. Such applications include, but not limited, homeland security to detect trace chemicals of explosives, biochemical weapons and illegal drug smuggling; food and drinking materials safety to detect pesticide residues; early disease diagnosis; environmental monitoring; industrial process monitoring, and so on.

In applications of the second category, the laser beam will strike on sample under test; the scattering light is collected from sample directly. It is normal Raman scattering and no sensor needed. Such technology is available, but is normally ignored and has not yet been implemented in applications include, but not limited to applications to detect counterfeit merchandise such as milk based powder with less protein; authentication for gem certification, content analyses of medical tablets, and detection of methanol and ethanol content in wines.

These and other objects and advantages of the present invention will no doubt become obvious to those of ordinary skill in the art after having read the following detailed description of the preferred embodiment, which is illustrated in the various drawing figures.

BRIEF DESCRIPTION OF THE DRAWINGS

The following drawings, which are incorporated in and from a part of the specification, illustrate embodiments of the present invention and, together with the description, serve to explain the principles of the invention.

FIGS. 1A-1C illustrate exemplified configurations of trace chemical detection using Surface-Enhance Raman Scattering.

"FIG. 16A-16D, 16G, and 16H are cross-sectional views of the nanostructure formed on the multi-layer layer structure after the fabrication process.

FIG. 16E and 16F are top views of the nano-structure formed on the multi-layer layer structure after the fabrication process.

DETAILED DESCRIPTION OF THE EMBODIMENT

Figure 2:
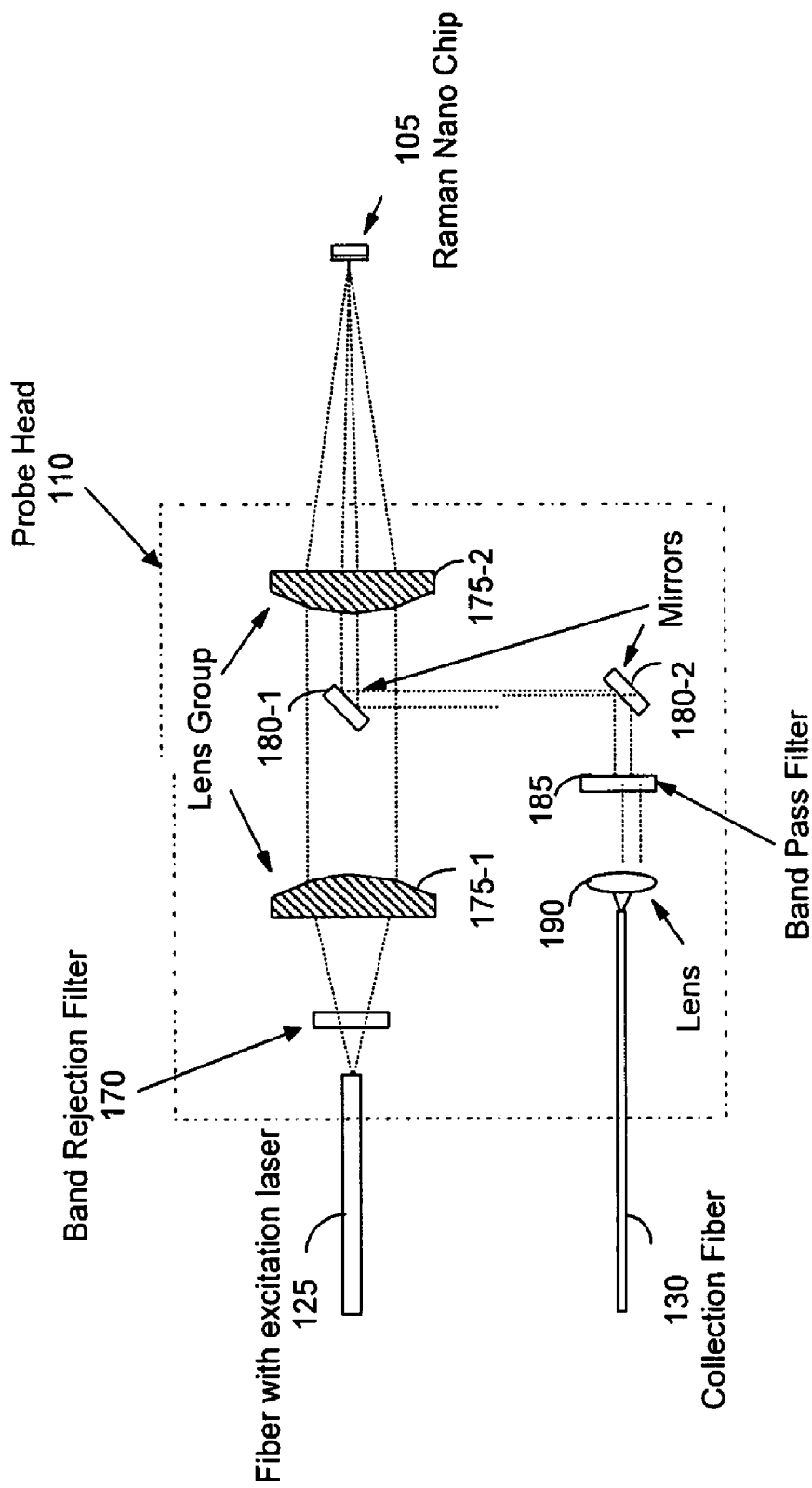
FIG. 2 A illustrates an exemplified design of a probe head for Raman scattering probe.

Referring to FIG. 1A, a light scattering probe 100 includes a probe head 110 and a sensor 105 (such as a RamanNanoChip™). As shown in FIG. 1B, a sensor 105 includes a plurality of nano rods 108 (or holes). A body fluid is obtained from a patient or an illicit drug user and applied to the sensing surfaces of the sensor 105. Examples of the body fluid can include blood, saliva, urine, serum, tear, sweat, and stomach fluid. The probe head 110 and the Sensor 105 are enclosed in a probe assembly 120. The probe assembly 120 can be depressurized by a vacuum pump to reduce contamination of the sensing surfaces for foreign substance.

A laser beam emitted by a laser 141 is guided by optical fibers 125 to illuminate the sensor 105, as shown in FIG. 1C. The probe head 110 is positioned adjacent to the sensor 105. In the present application, the term RamanNanoChip™ refers to a sensor comprising a nano-scale surface structure that is configured to adsorb molecules of a chemical, biological, or medical sample for detecting using a light scattering probe. The scattered light is collected by the probe head 110 and guided to a spectral analyzer 150 along by an optical fiber 130. A Raman spectrum of the scattered light is obtained by the spectral analyzer 150. The spectral signatures in the Raman spectrum are identified and to compared with database of spectral signatures for various molecules. An output signal can indicate identification of a disease when a threshold of certain molecules under detection is exceeded. In the present specification, the term "spectral signature" can refer to one or more spectral peaks, one or more spectral valleys, and other spectral shapes such as relative peak height, peak line width, peak shape, etc., that characterize one of more molecular bonds in a biological, medical, or chemical materials.

Referring to FIG. 2, the probe head 110 can receive a laser projection from an input laser fiber 125 to pass through a band ejection filter 170 to pass through a lens group 175-1 and 175-2 to project onto sensor 105. A scattering light is projected back to a group of mirrors 180-1 and 180-2 to pass through another band-pass filter 185 and a collimated lens to output from the collection fiber 130.

Figure 3A:
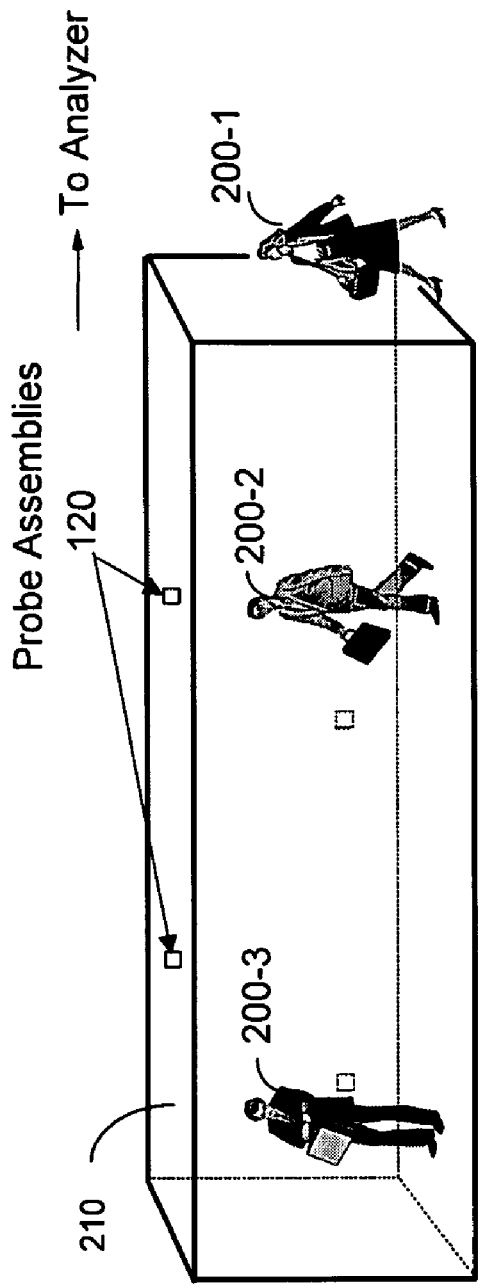
FIGS. 3A and 3B are schematic diagrams respectively showing inspections of passengers and luggage using a Raman scattering probe at an airport.

FIG. 3A is a schematic diagram to show a configuration of the Surface Enhance Raman Scattering application in safety of transportation and other places where a passenger screening is required to monitor passengers 200-1, 200-2, and 200-3. For passenger screening, the probe assembly 120 with embedded sensor 105 is placed in the passageway 210. The probes head 120 are connected by fibers to the spectral analyzer 150 in office near or far away from it. The probe head 120 is aligned to point to the sensing surface of a sensor 105 and they are packaged together. The passageway tunnel 210 can be forced ventilated and under little negative pressure and/or little higher temperature to increase evaporation of harmful materials. If a passenger, e.g., passenger 200-2, carrying explosive materials, harmful chemicals, chemical weapons, bio-chemical weapons, nuclear weapons or narcotic drugs, few molecules of such materials will volatilize into air that molecules are adsorbed onto the surface of a sensor through specially designed sample collection system. The Raman Spectrum will be recorded and compared with database in mainframe at office. As soon as the harmful materials are detected, early stage alarm signal will be triggered and appropriate security actions can be further processed.

Figure 3B:
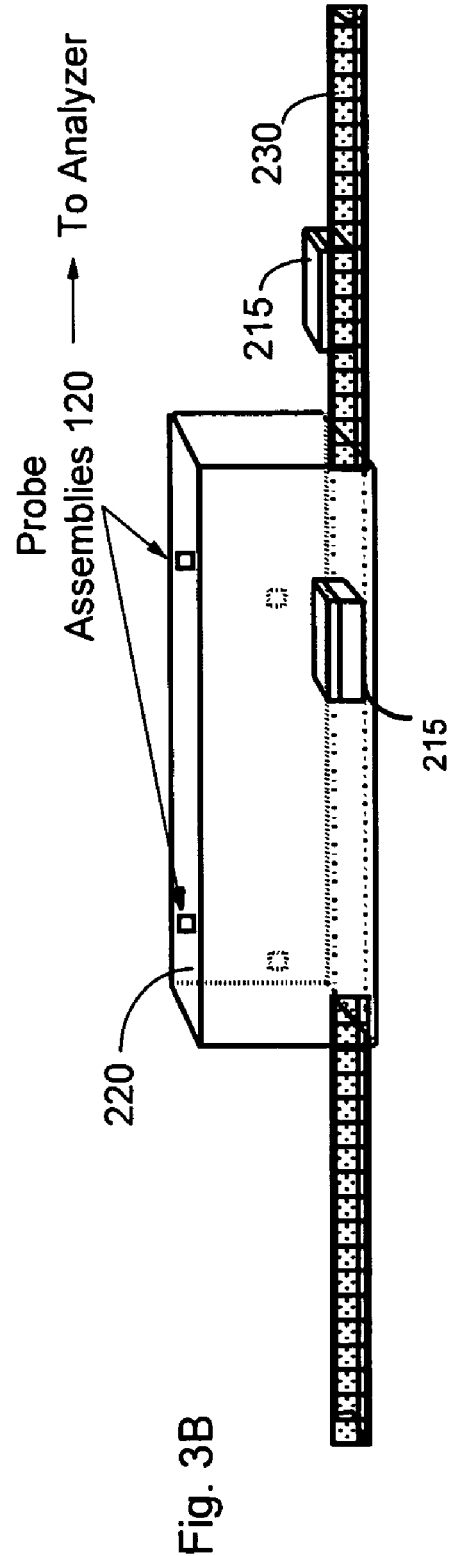

FIG. 3B is a diagram to show application implemented to monitor luggage 215 for freight transportation carried by a conveyer 230 to pass through cargo screening channel 220. The probe assembly 120 with embedded sensor 105 is placed around the cargo screen channel 220. The probes head 120 are connected with fibers to the spectral analyzer 150 in office near or far away from it. The probe head 120 is aligned to the surface of a sensor 105 and they are packaged together to detect any explosives, chemical or biochemical weapon, or harmful chemicals enclosed in the luggage 215. This configuration can be implemented in other applications such as mail stations, railway stations, custom inspection areas, traffic control zones, etc. This configuration can be easily implemented to detect gun powders or other explosives or hazardous materials.

Figure 4:
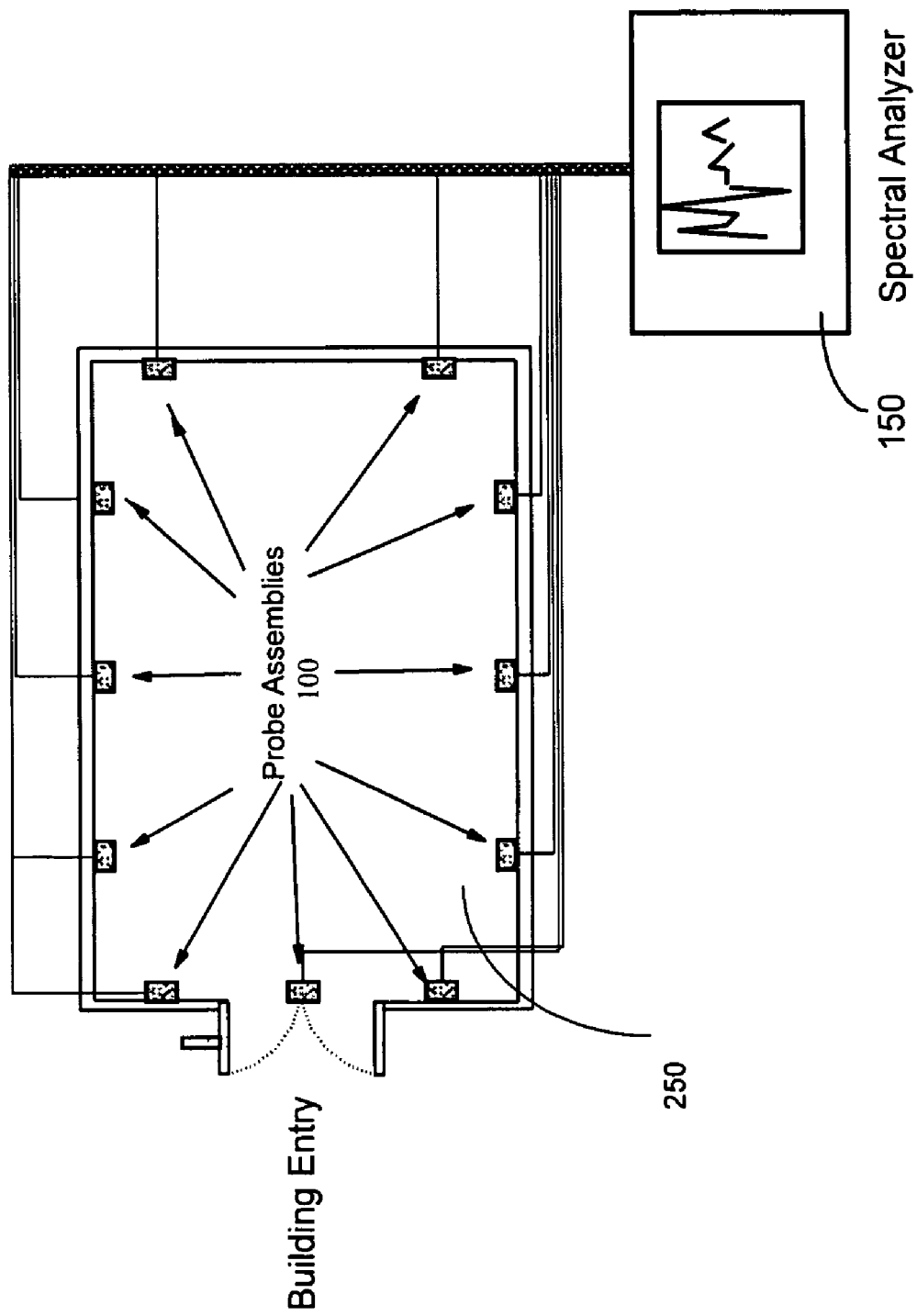
FIG. 4 is a schematic diagram showing safety monitoring in public building safety using a Raman scattering probe.

FIG. 4 is schematic diagram of Surface Enhance Raman Scattering applications using a sensor in safety of public buildings 250 such as airport, railway or bus stations, ballpark buildings, Federal buildings, auditoriums, theaters, courthouses, and other public buildings. The light scattering probe 100 that includes probe head 120 combined with a sensor 10 are distributed in the public buildings or others protected areas. The light scattering probes 100 are applied to monitor many different molecular substances to provide earlier detection of any dangerous or harmful chemicals enter into the monitor areas. Particular examples of hazardous material monitoring include, but not limited to detection of explosive materials, chemical or biochemical weapons including anthrax, drugs, and so on.

Figure 5:
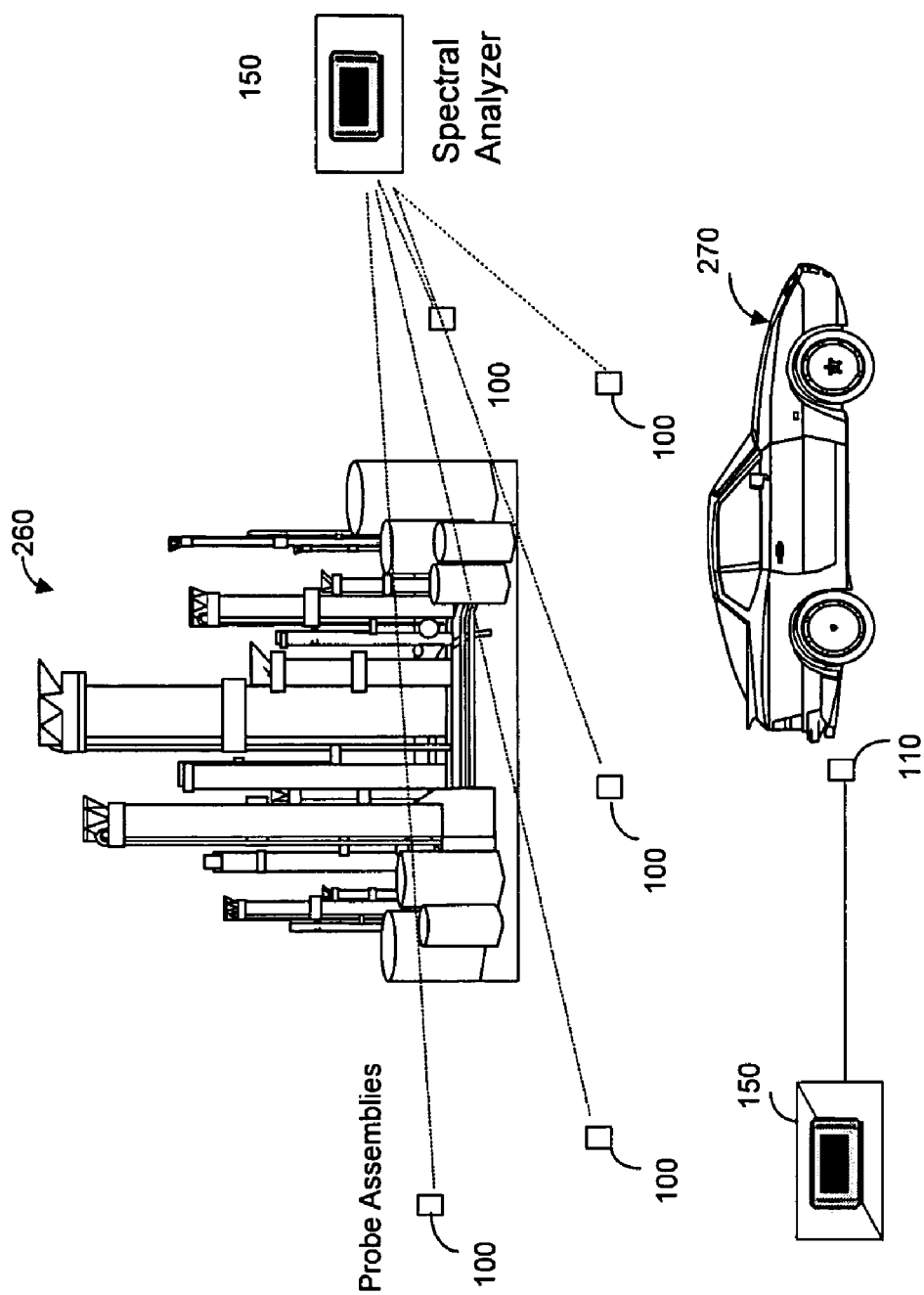
FIG. 5 is a schematic diagram showing environmental monitoring using a Raman scattering probe.

FIG. 5 is schematic diagram of applying the technology of Surface-Enhance Raman Scattering using a sensor to monitor harmful chemicals released into the environment. The light scattering probes 100 are distributed around potential pollution source, e.g., a factory 260 or around highway where great number of automobiles 270 pass through. The light scattering probes 100 distributed around the monitored areas generate Raman scattering light that is transmitted to a mainframe spectrum analyzer 150 to determine the contents and concentration of substance released into the environment. The monitoring sample can be, but not limited, soil, water, lake, river, seashore, well, plants, etc. This application can be extended to car exhausted gas detection and monitoring by placing the probe assembly near by car exhausting output.

Figure 6:
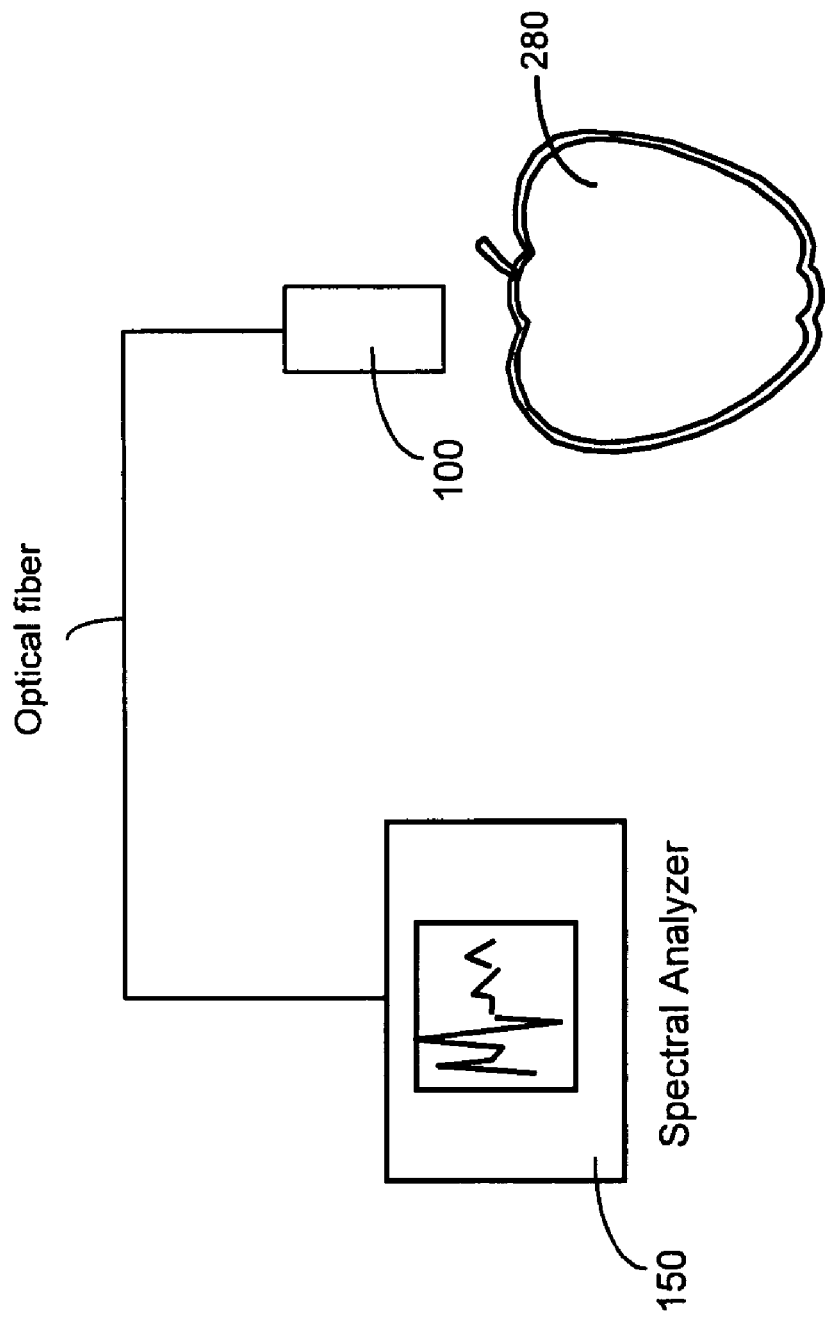
FIG. 6 is a schematic diagram showing inspection of food safety using a Raman scattering probe.

FIG. 6 is schematic diagram of applying the technology of Surface Enhance Raman Scattering using a sensor to monitor substances for inspecting quality and safety of foods. The light scattering probes 100 is placed close to a food item 280, i.e., an apple or different fruits, vegetables or other food items that could be contaminated through transportations, food processing, or even food growth process. The molecules of residue pesticide or other contaminations are drawn into the light scattering probe 100. A sensor is used to detect any suspect harmful chemicals contained in the food.

Figure 7:
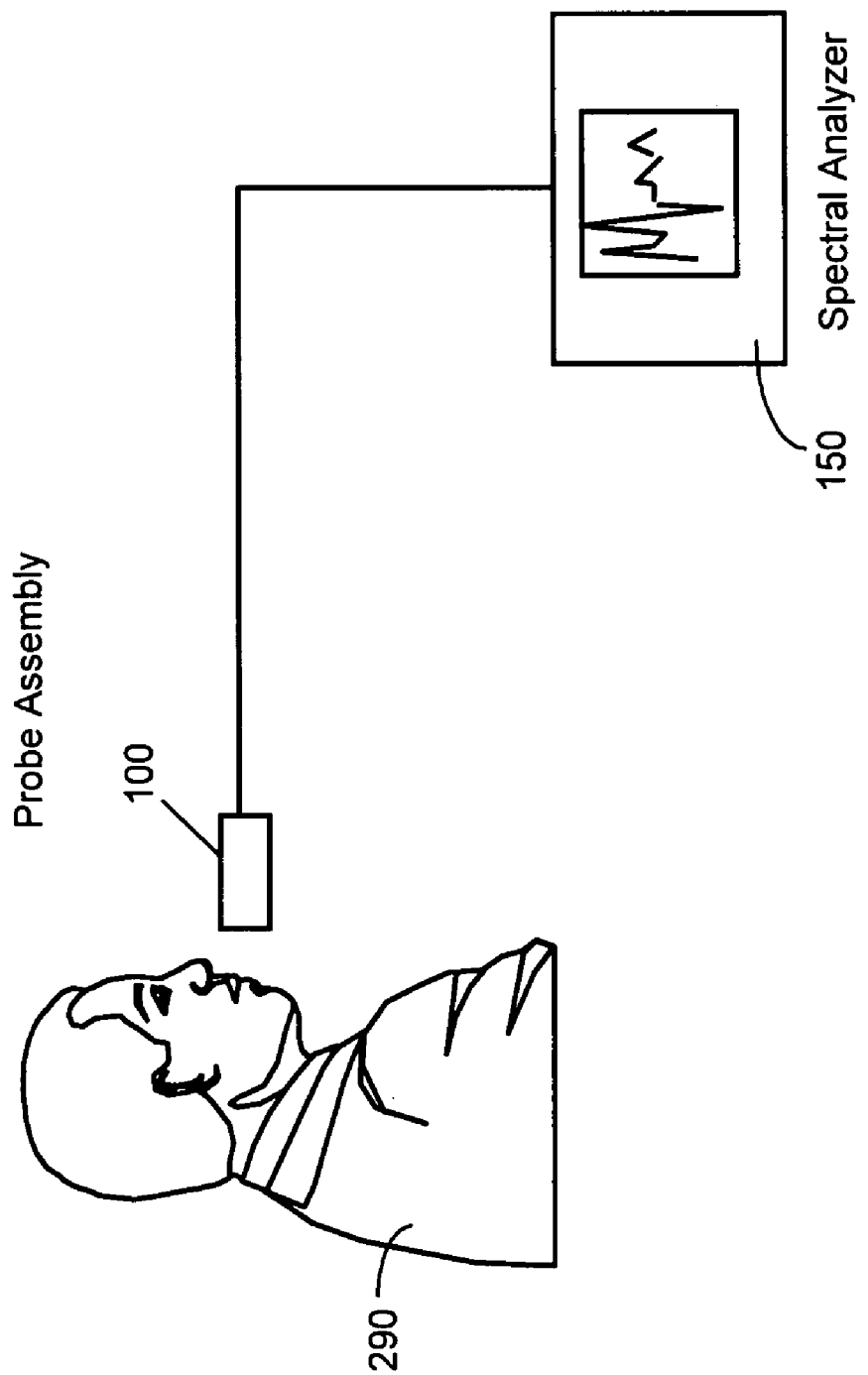
FIG. 7 is a schematic diagram showing disease diagnosis and biomedical detection using a Raman scattering probe.

FIG. 7 is schematic diagram of applying the technology of Surface Enhance Raman Scattering with or without using a sensor to monitor substances for early decease detection and diagnosis. The light scattering probe 100 is placed near a patient 290. Research result indicated that human breathed air have special chemicals contained, such as alkenes and benzene derivatives, if a person under screening is associated with disease, such as lung cancer. Raman sensing technology is able to fingerprint those chemicals in breath test to identify some special diseases such as cancers. The light scattering probe 100 is placed near the patient for carrying out a physical examination. The patient blows the outpoured breath-air to the light scattering probe 100. The sensor in probe assembly receives the inlet air for generating a Raman scattering light corresponding to the molecules contained in the airflow from the patient. The scattering lights are collected by probe head and sent to the spectral analyzer 150 to generate Raman spectrum. Breath test with Raman sensing technology is to make early disease diagnosis which disease includes, but not limited to lung cancer, breast cancer, stomach cancer, Liver cirrhosis, failing kidney, ulcer cancer, etc. In case of testing human body fluids, the fluid is dropped on a sensor manually, or Raman sensing device can be designed to connect to toilet for easy sample collection as smart toilet to timely monitor abnormal signals for disease and drug detection This application also includes identifying and sorting protein, DNA and RNA. All testing samples in above applications can be placed in contact with a sensor to enhance the sensitivity and intensity of Raman scattering detections. The RamanSensor can also be applied to other areas, including but not limited to identify Alzheimer's disease, non-invasively test glucose to monitor diabetes, non-invasive test carotenoids to monitor antioxidant status for early cancer screening purpose, and so on.

Figure 8:
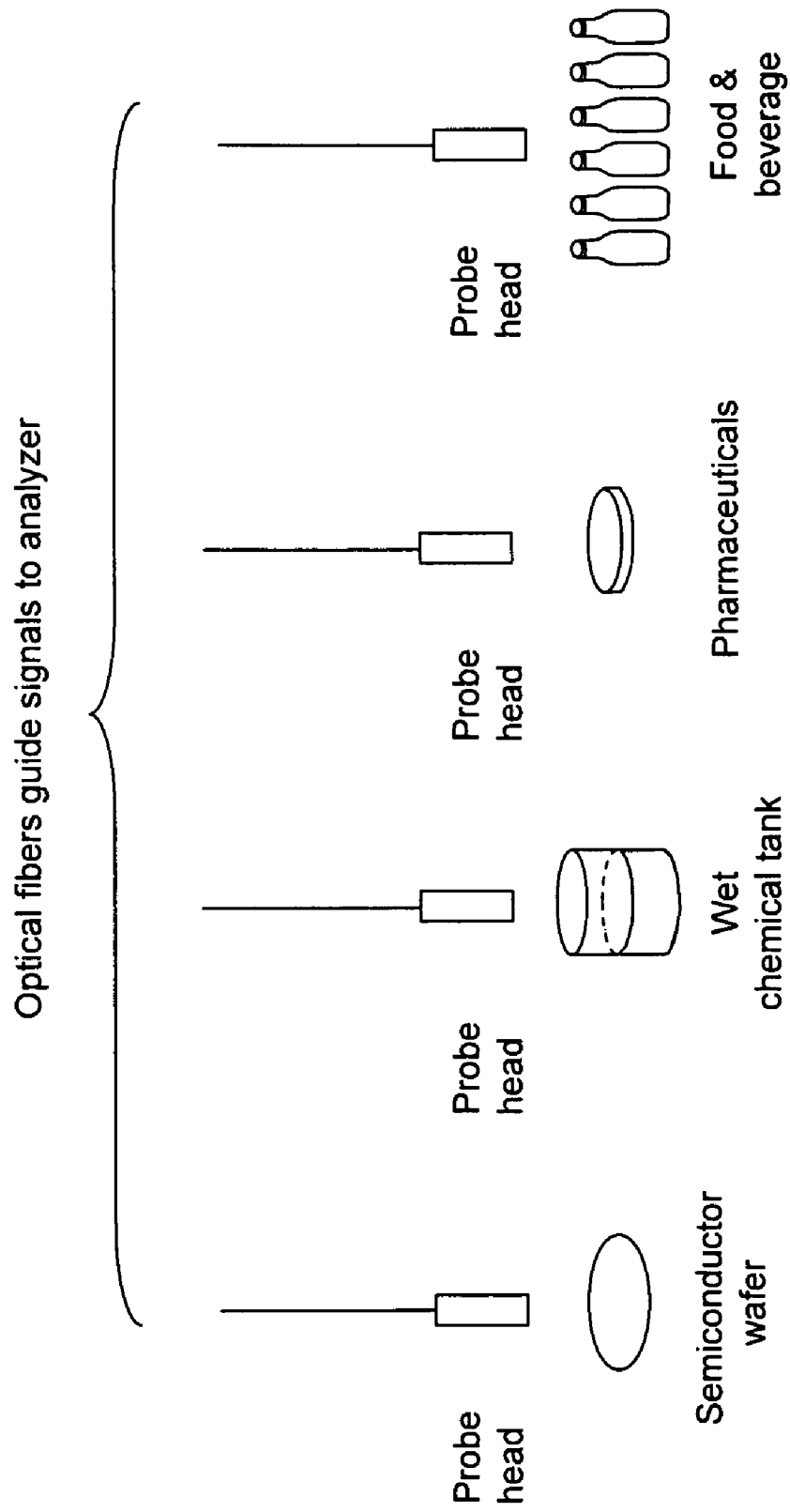
FIG. 8 is a schematic diagram showing manufacture quality control with and without a Raman scattering probe.

FIG. 8 is schematic diagram of Raman scattering application in industrial quality control with or without a sensor such as a RamanNanoChip™. The applications include, but are not limited to, the in-line monitoring wet chemical concentration in wet chemical process line, stand-off monitoring of sealed chemical tanks, remote trace chemical detection, semiconductor wafer defect evaluation, and monitoring of the food, fruit and vegetable storage, etc.

Figure 9:
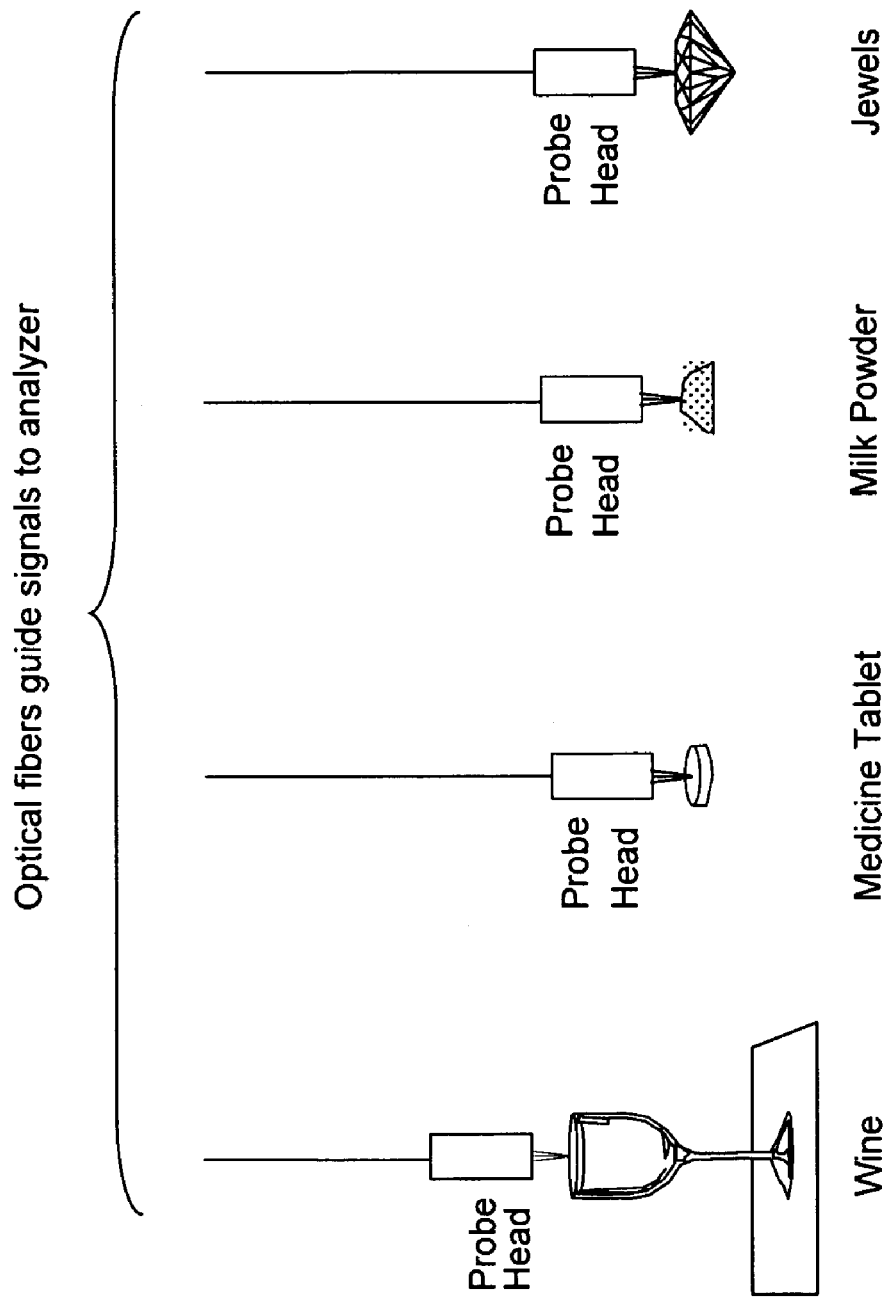
FIG. 9 is a schematic diagram showing detection of counterfeit merchandise, drug screening and non-invasive in-vivo test glucose for monitoring diabetes using a Raman scattering probe.
Figure 10:
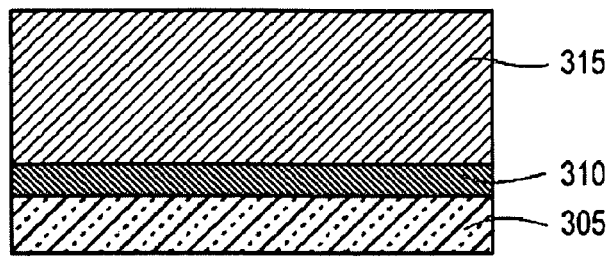
FIG. 10 is a cross-sectional view of a multi-layer layer structure to be used for fabricating a nano-structure.
Figure 11B:
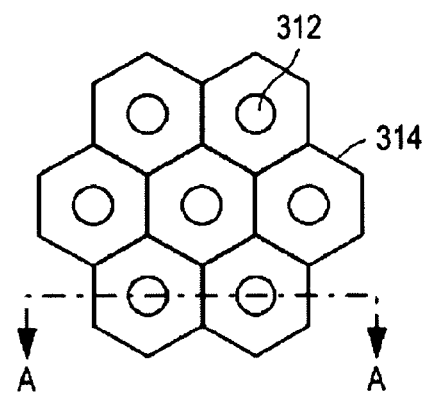
FIG. 11B is a top view of the multi-layer layer structure of FIG. 11A.
Figure 11A:
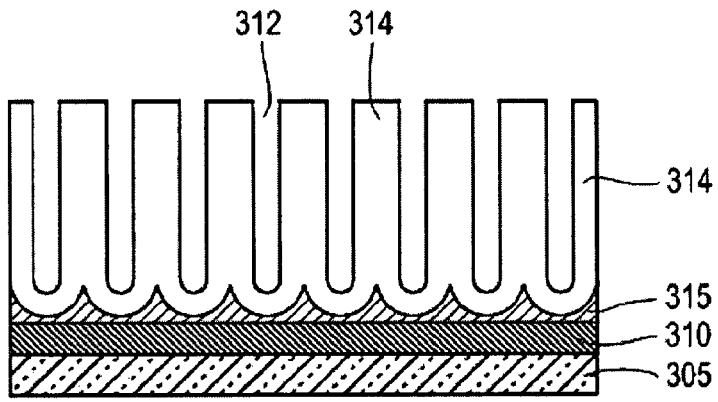
FIGS. 11A is a cross-sectional view showing the formation of holes by anodization in the multi-layer layer structure of FIG. 10.
Figure 11C:
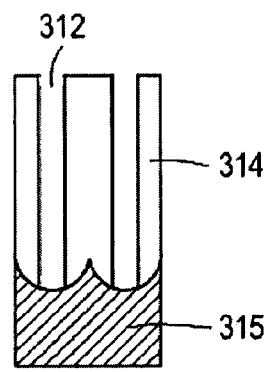
FIG. 11C is a cross-sectional view of the multi-layer layer structure along the line A-A in FIG. 11B.
Figure 12:
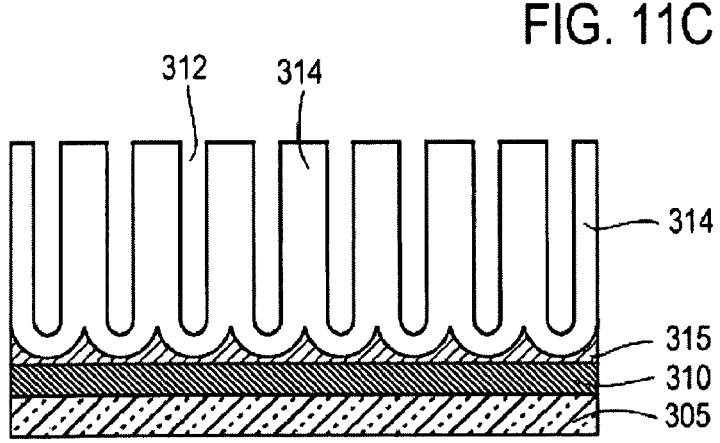
FIG. 12 is a cross-sectional view of the nano-structure formed on the multi-layer layer structure after a wet chemical etch or chemical mechanical polishing (CMP).

FIG. 9 is schematic diagram of applying the technology of Surface Enhance Raman Scattering to identify and screen materials including, but not limited to detect counterfeit merchandise. The applications may include operations such as food, drug and medicine screening. In theses cases, a sensor may or may not be required. The excitation laser directly strikes on samples under test. With improvement of the whole system of Raman Spectroscope, new applications that might not be available previously are now become practical. The Raman Spectrum of scattering light from the tested materials shows characteristic contents thus provide clear indications whether there are illegal additives added to the commercial merchandises. The potential counterfeit merchandise such as milk-based powder, wine, and medical tablets may be placed under the Raman detector as materials under investigation and screen. The applications can be extended to authenticated signatures and currency bills by detecting false signature and false bills by generating Raman scattering spectrum of the signature and dollar bills and compare these spectrum with measurements obtained from authenticated signature and dollar bills.

FIGS. 10 to 15 show a series of processing steps for fabricating a nano-structured noble metal surface of this invention. A multi-layer structure 302 (FIG. 10) includes a substrate 305, a conductive layer 310, and an aluminum oxide layer 3 15. The substrate 305 can for example be n-type silicon flat wafer (3-8 Ω-cm) or oxidized (30-50 nm SiO2) p-type silicon (5-10 mΩ-cm). The conductive layer 310 can include Ti and Ni and is deposited on the substrate 305 and can be electrically and thermally conductive. The thickness of the conductive layer 310 can be optimized to provide i) adhesion to a subsequently deposited noble metal film, such as Ag, or Au film, etc., ii) electrical conductive film to apply electrical bias to sensing surface in field application, iii) thermal conductive layer to apply lower temperature of sensing surface. The thickness of the conductive layer 310 can be typically controlled in the range of 100 Å-1,000 Å. Then The aluminum layer 315 is deposited on the conductive layer 310. The aluminum layer 315 can have a purity of 99.999% and thickness in the range of 1.0-10.0 μm. The substrate 305, the conductive layer 310, and the aluminum oxide layer 315 are annealed at 400° C.-500° C. in a $N_2$ purged furnace for 2-5 hours to recrystallize the Al film. Anodization is then conducted to produce a porous structure in a form of porous aluminum oxide layer 315 as that shown in FIGS. 11A and 11B. A porous structure is formed on the aluminum oxide layer 315 wherein the porous structure includes a plurality of pores 312 surrounded by walls 314 with the cross section view along a horizontal line A-A shown in FIG. 11C. Then wet oxide etch process is carried out in FIG. 12 to remove both top porous $Al_2O_3$ layer and barrier layer. A second anodization is carried out to consume all Al metal so that the barrier layer and top porous $Al_2O_3$ layer are right above the conductive metal layer.

Figure 13:
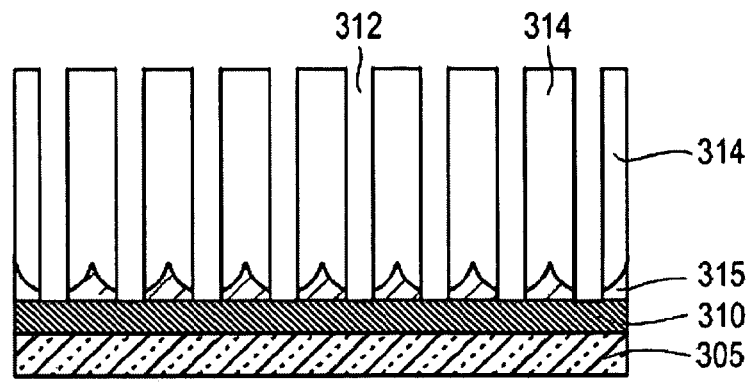
FIG. 13 is a cross-sectional view of the nano-structure formed on the multi-layer layer structure after the removal of the barrier layer at the bottom of the holes and etching down to the conducting layer.

In FIG. 13, an oxide etching is carried out to remove the barrier layer at the bottom of the pores and to widen the pore diameter. The wet etch process allows the pores 312 to extend downward to reach the conductive layer. The thickness of the resulted porous oxide layer can be controlled by controlling the processing parameters of aluminum physical vapor deposition (PVD); anodization and the subsequent wet etch processes. The self-assembled pore structure is naturally formed with a hexagonal array. The pore diameter (d) and the inter-pore distance (D) can depend on applied anodization voltage (V), current density (i) and the properties of the electrolyte, and the subsequent pore widening wet etch process.

Figure 14A:
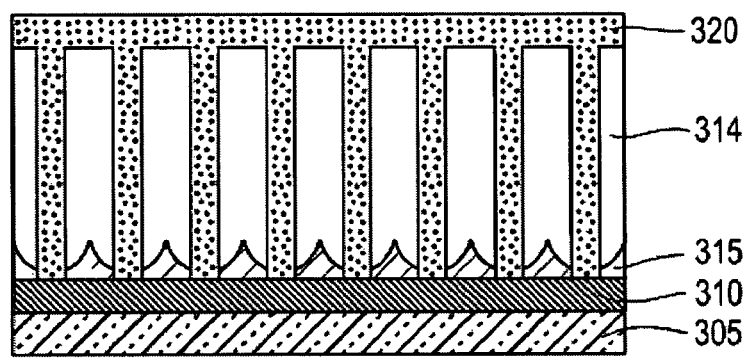
FIG. 14A is a cross-sectional view of the nano-structure formed on the multi-layer layer structure after the deposition of a noble metal.
Figure 14B:
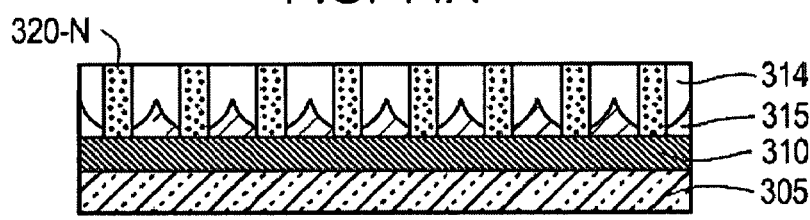
FIG. 14B is a cross-sectional view of the nano-structure formed on the multi-layer layer structure after the removal of the noble metal on the top layer.
Figure 15:
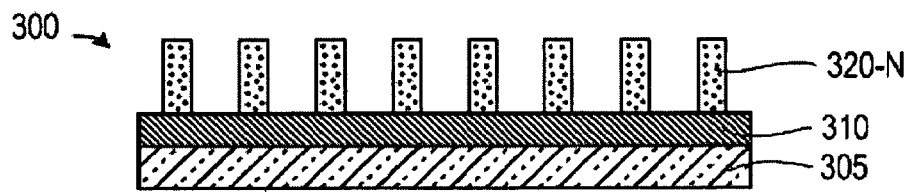
FIG. 15 is a cross-sectional view of the nano-structure formed on the multi-layer layer structure after the oxide layer is removed.

Referring to FIG. 14A, a noble metal such as Ag is deposited on the porous layer 315 to fill the pores 312 and to form a layer 320. The layer 320 can be formed by PVD process or electroplating. In FIG. 14B, a layer of the noble metal 320 is removed while leaving the noble metal 320-N in the pores 312. Another wet metal etch or CMP process is applied further control height of the noble metal 320-N filling the pores. In FIG. 15, the aluminum oxide 315 and the residue aluminum film 315-AL at the bottom of the porous aluminum layer 315 are removed to form a nano-structured surface 300 comprising an array of nano rods 320-N.

The nano rods 320-N are substantially straight and are perpendicular to the substrate 305 and the conductive layer 310. The nano rods 320-N can have substantially the same or similar widths. The neighboring nano rods 320-N are separated by gaps that remain substantially constant at different distances from the conductive layer 310.

The geometries of the photolithographic masks applied in the above-described fabrication processes are designed to match the expected size of the sensing chip and the area of the metal pad, which locates at the corner of the chip. For field applications, the chemical detection sensing chips are formed as packaged sensing chips by applying different semiconductor packaging technologies, e.g., wire-bonding, flip-chips, system-on chip (SOC), etc., that will be further described in a different Patent Application.

In some embodiments, nano-structures can be fabricated by a different process as shown in FIGS. 16A to 16F. A two-layer structure 362 includes a conductive layer 335 and a substrate 330. The conductive layer 335 can be made of titanium (Ti) or nickel (Ni), and can be electrically and thermally conductive. The substrate 330 can be an n-type silicon flat wafer (3-8 Ω-cm) or oxidized (30-50 nm $SiO_2$) p-type silicon flat wafers (5-10 mΩ-cm). The thickness of this conductive metal layer 335 can be controlled in the range of 100 Å-1,000 Å. An adhesion layer (e.g. made of Ag) can be deposited to the metal layer 335. The thickness of the conductive layer 335 can be optimized for applying an electric bias to the sensing surface for trace chemical detection and further for applying a lower temperature to the sensing surface to enhance sensitivity of trace chemical detection.

In FIG. 16B, a noble metal layer 340 is deposited on top of the conductive layer 335. The noble metal may be a silver layer, e.g., Ag layer having a thickness of 10-200 nm. In FIG. 16C, a second metal layer 345 is deposited on top of the noble metal layer 340. The second metal layer 345 can include aluminum with a 99.999% purity and a thickness in the range of 1.0-10.0 μm. The aluminum layer 345 is then annealed at 400° C.-500° C. in a $N_2$ purged furnace for 2-5 hours to recrystallize the Al film.

In FIG. 16D, an anodization process is carried out to produce a porous structure in a form of porous aluminum oxide 345'. A top view is shown in FIG. 16E where the porous structure is formed with naturally self-assembled hexagon-shaped nano pore-array that includes a plurality of pores 348 surrounded by hexagon-shaped pore wall 349. Neighboring pores 348 have a center-to-center distance D. After removing top anodized layer and the barrier layer by a wet chemical process, a second anodization process is carried out to consume all Al metal so that the barrier layer and top porous $Al_2O_3$ layer 345' are right above the noble metal layer 340. Then a wet etch process is performed to widen the pores 348 and to remove the barrier layer at the bottom of the pores 348. As the wet etch process proceeds, as shown in FIG. 16F, the pores 348 are widened and the walls 349 surrounding the pore become thinner. The etch process can be controlled to form a plurality of nano-holes 348 surrounded by wall 349. Alternatively, the etching of the pores 348 can widen the pores 348 so much such they touch each other, which can produce a hexagonal array of quasi-triangle nano columns 349'.

In FIG. 16G, the noble metal layer 340 is etched down and the pores 348 are extended downward to reach the conductive titanium layer 335. In FIG. 16H, a wet oxide etch is performed to remove the aluminum oxide followed by a wet metal etch to remove the aluminum residue at the bottom of the pores 348. The aluminum oxide 315 and the residue aluminum film 315 at the bottom of the porous aluminum layer 315 are removed to form an array of nano rods 349' having controlled heights, diameters and well-defined inter-rod distances. The array can have quasi-triangle periodic cells.

The nano rods are substantially straight and are substantially perpendicular to the substrate 330 and the conductive layer 335. The nano rods can have substantially the same or similar widths. Neighboring nano rods are separated by gaps that remain substantially constant at different distances from the conductive layer 335.

Figure 17:
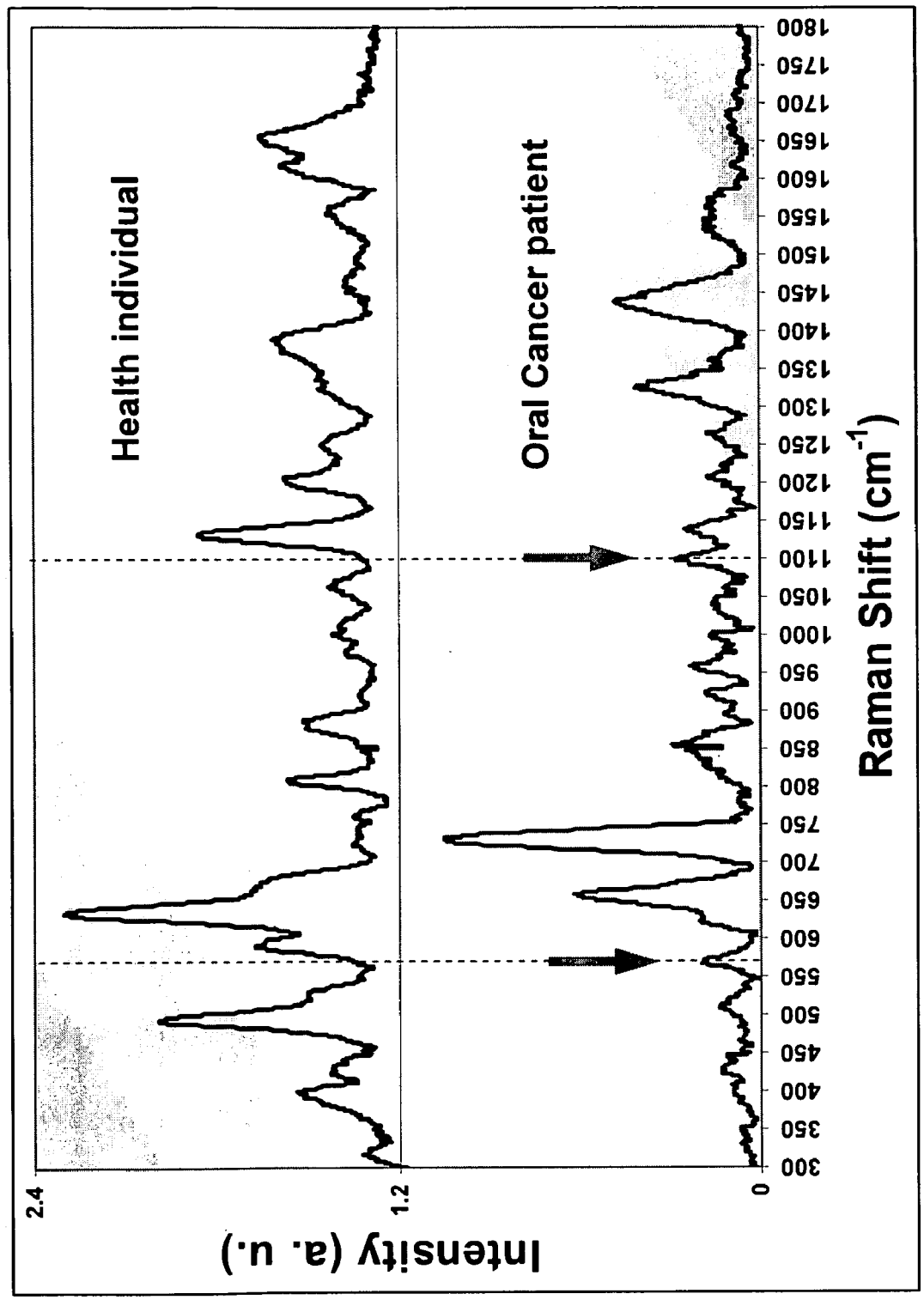
FIG. 17 illustrates an exemplified Raman spectral signature for oral cancer detected in the serum of an oral cancer patient by the disclosed Raman scattering probe.

In some embodiments, diseases can be identified by analyzing Raman spectra obtained from body fluids from a patient using the light scattering probe 100 as described above. Referring to FIG. 17, the Raman spectrum obtained from a saliva sample from an oral cancer patent has show two signature spectral peaks respectively around, for example, 560 cm$^{-1}$ (in the region from 540 cm$^{-1}$ to 570 cm$^{-1}$) and 1100 cm$^{-1}$ (in the region from 1185 cm$^{-1}$ to 1105 cm$^{-1}$) which are absent in a healthy individual without the oral cancer. The signature spectral peaks at 560 cm$^{-1}$ and 1100 cm$^{-1}$ are associated with molecular vibrations for C—S, S—S, and O—P—O (PO$_2$) bonds in, for example, cysteine, ATP, and ADP. The identification of these spectral signatures can include the steps: a spectral band is first selected at Raman peaks with Raman shift in unit of cm$^{-1}$ (wavenumber) of each spectral signature. A background scattering intensity level is determined. The peak intensity level, relative intensity or integrated area of the peak, is calculated. A signal-to-noise ratio is calculated using the peak intensity and the background level. If the signal-to-noise ratio is higher than a predetermined threshold (e.g., 3 or higher), the spectral signature of a Raman peak is positively identified. The identification of spectral signatures for detecting diseases and drug use can be assigned by statistical analysis and several computation algorithms such as dendrograph classification and Principal Component Analysis. A patient can be diagnosed as likely having oral cancer or at an early stage of an oral cancer if spectral signatures around 560 cm$^{-1}$ and 1100 cm$^{-1}$ are both identified. Appropriate doctors and patients themselves may be alerted for further testing using the same or other types of diagnosis techniques.

Figure 18:
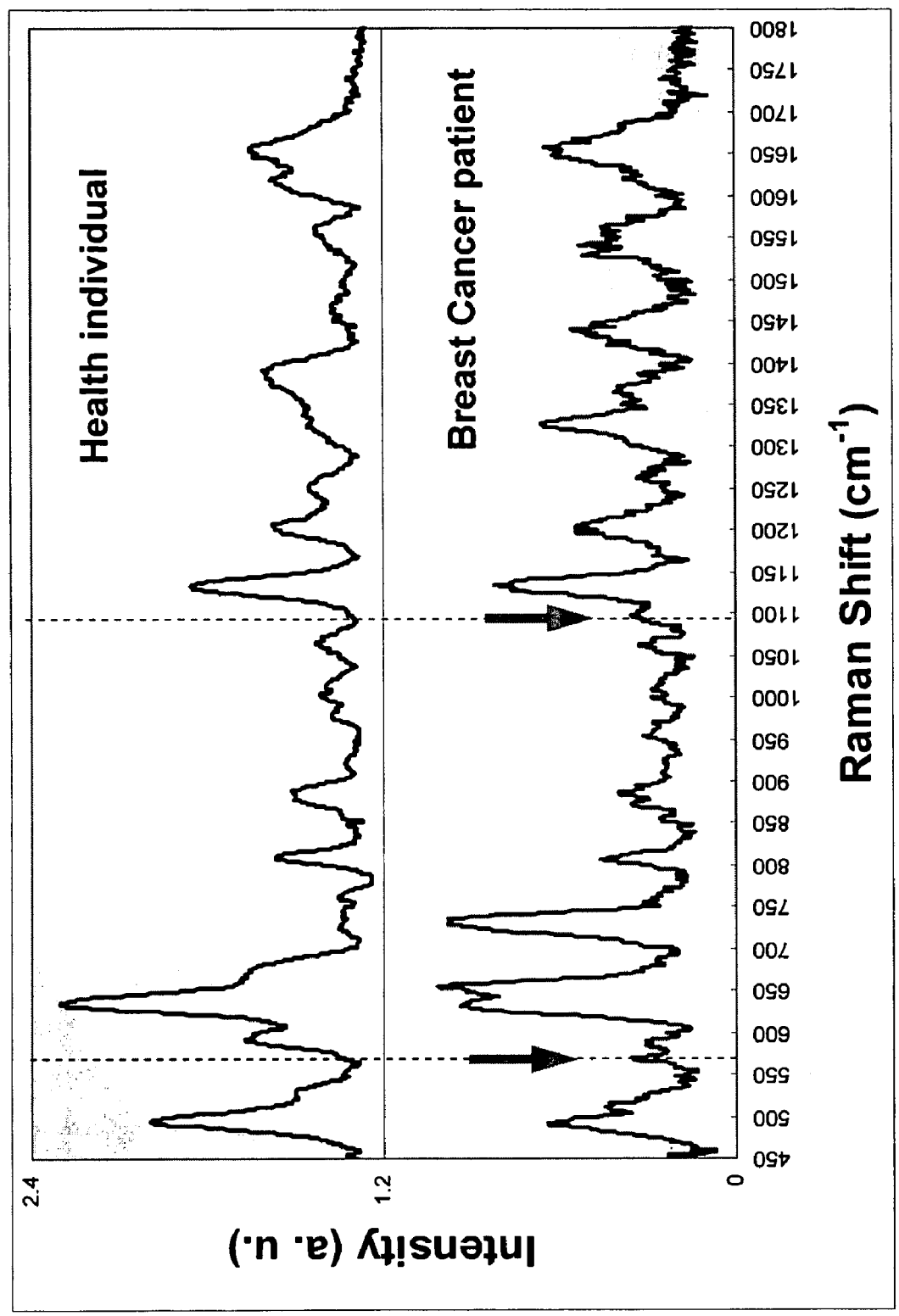
FIG. 18 illustrates an exemplified Raman spectral signature for breast cancer detected in the serum of a breast cancer patient by the disclosed Raman scattering probe.
Figure 19:
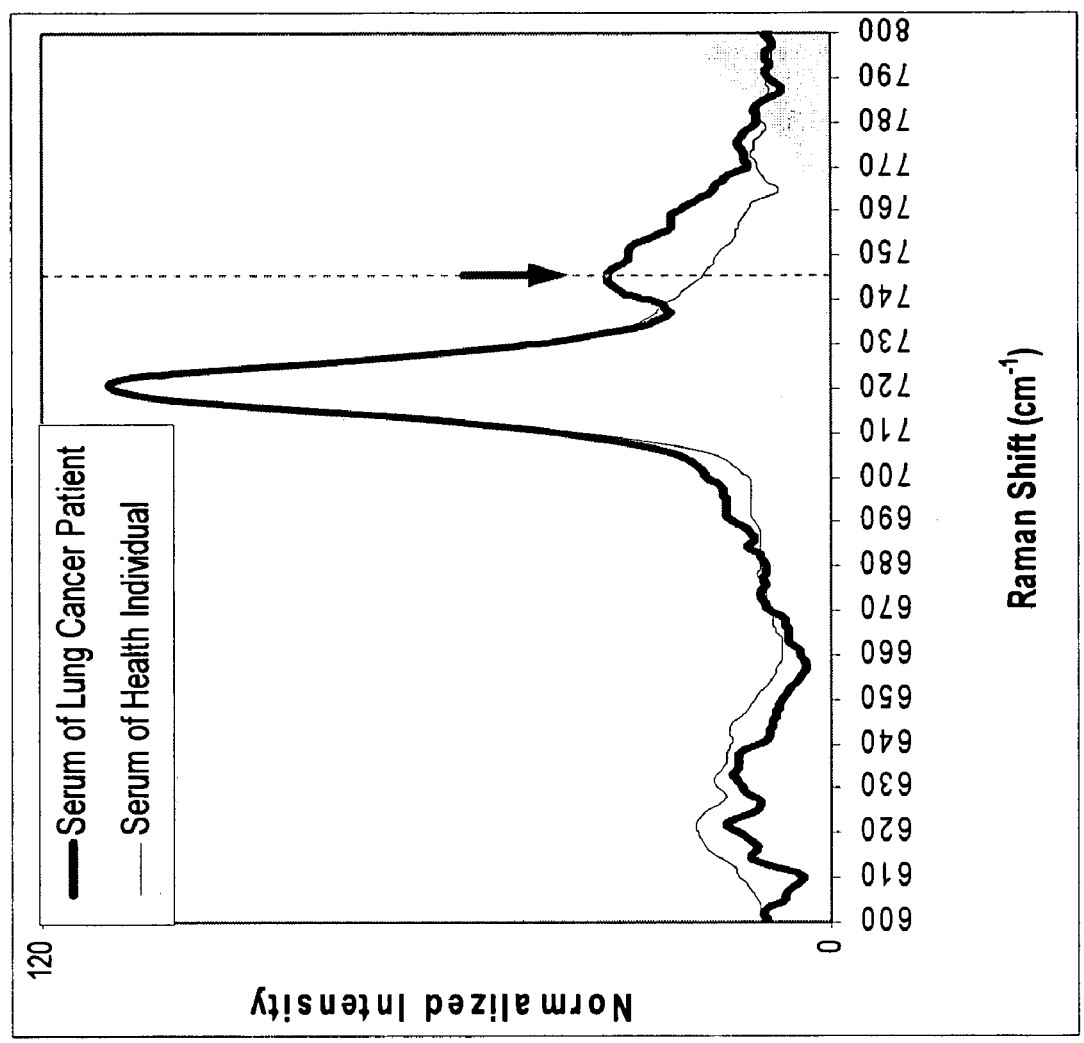
FIG. 19 illustrates an exemplified Raman spectral signature for lung cancer detected in the serum of a lung cancer patient by the disclosed Raman scattering probe.
Figure 20:
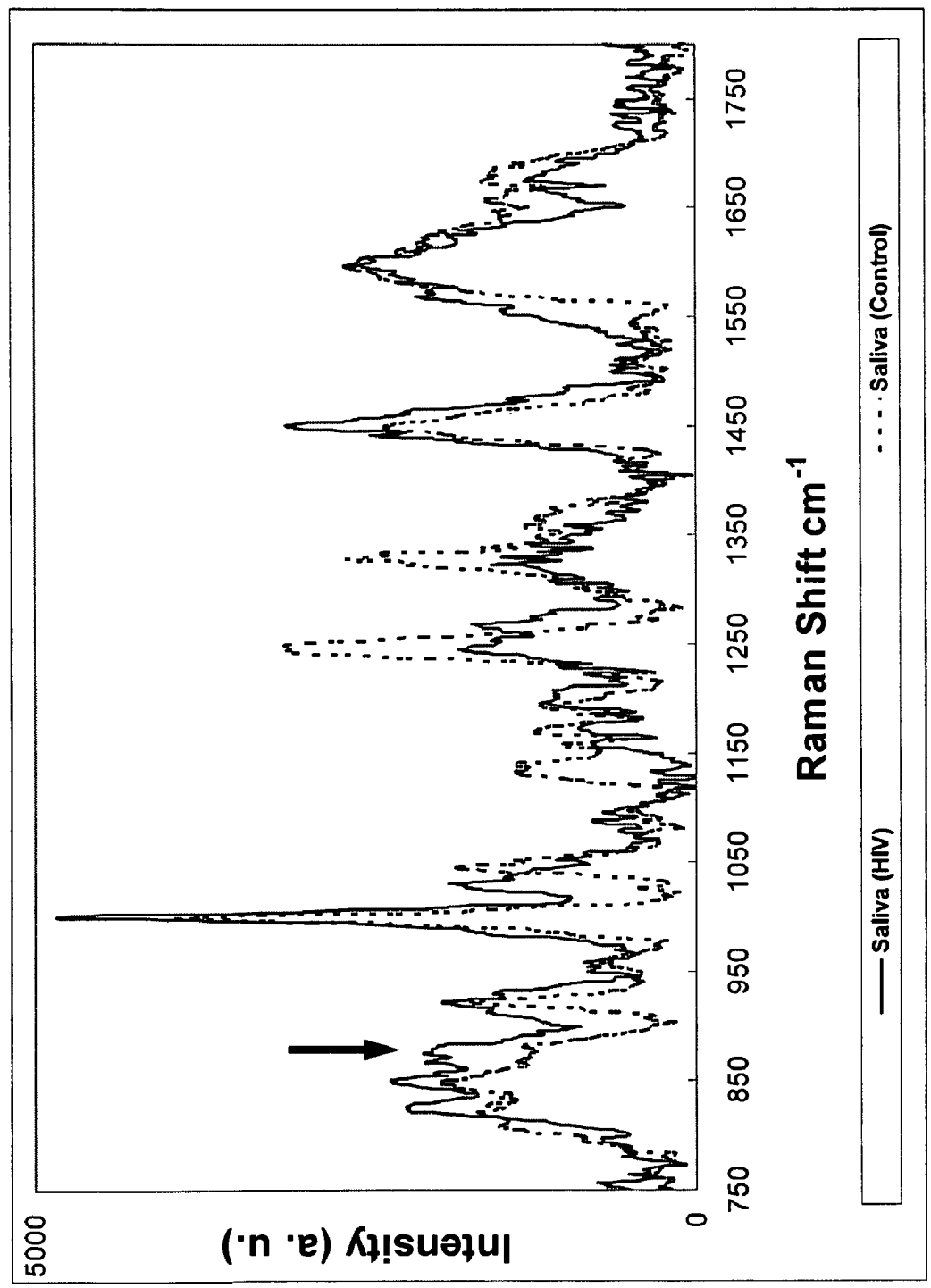
FIG. 20 illustrates an exemplified Raman spectral signature for HIV detected in the saliva of an HIV patient by the disclosed Raman scattering probe.

The disclosed systems and methods can also be used to estimate glucose level so that to evaluate diabetes status. A signature spectral peak in the region from 1115 cm$^{-1}$ to 1135 cm$^{-1}$, for example, 1124 cm$^{-1}$, which is associated with molecular vibration of glucose, in a Raman spectrum obtained from a saliva sample from a diabetes patient can provide key evidence for diagnosing diabetes. The intensity, relative intensity or integrated area of this Raman peak, can be used to evaluate glucose concentration of a body fluid from a patient to score potential diabetes level. Similarly, referring to FIGS. 18-20, breast cancer can also show spectral signatures in Raman spectrum obtained from saliva around 560 cm$^{-1}$ and 1100 cm$^{-1}$ (FIG. 18). Lung cancer can have a spectral signature in Raman spectrum obtained from a serum sample around 745 cm$^{-1}$ (FIG. 19). The signature spectral peak at 745 cm$^{-1}$ is associated with molecular vibrations for C—S bonds in phosphate, for example. HIV can have a spectral signature in Raman spectrum obtained from a serum sample in the region of 865 cm$^{-1}$-885 cm$^{-1}$, for example, around 870 cm$^{-1}$ (FIG. 20).

Figure 21:
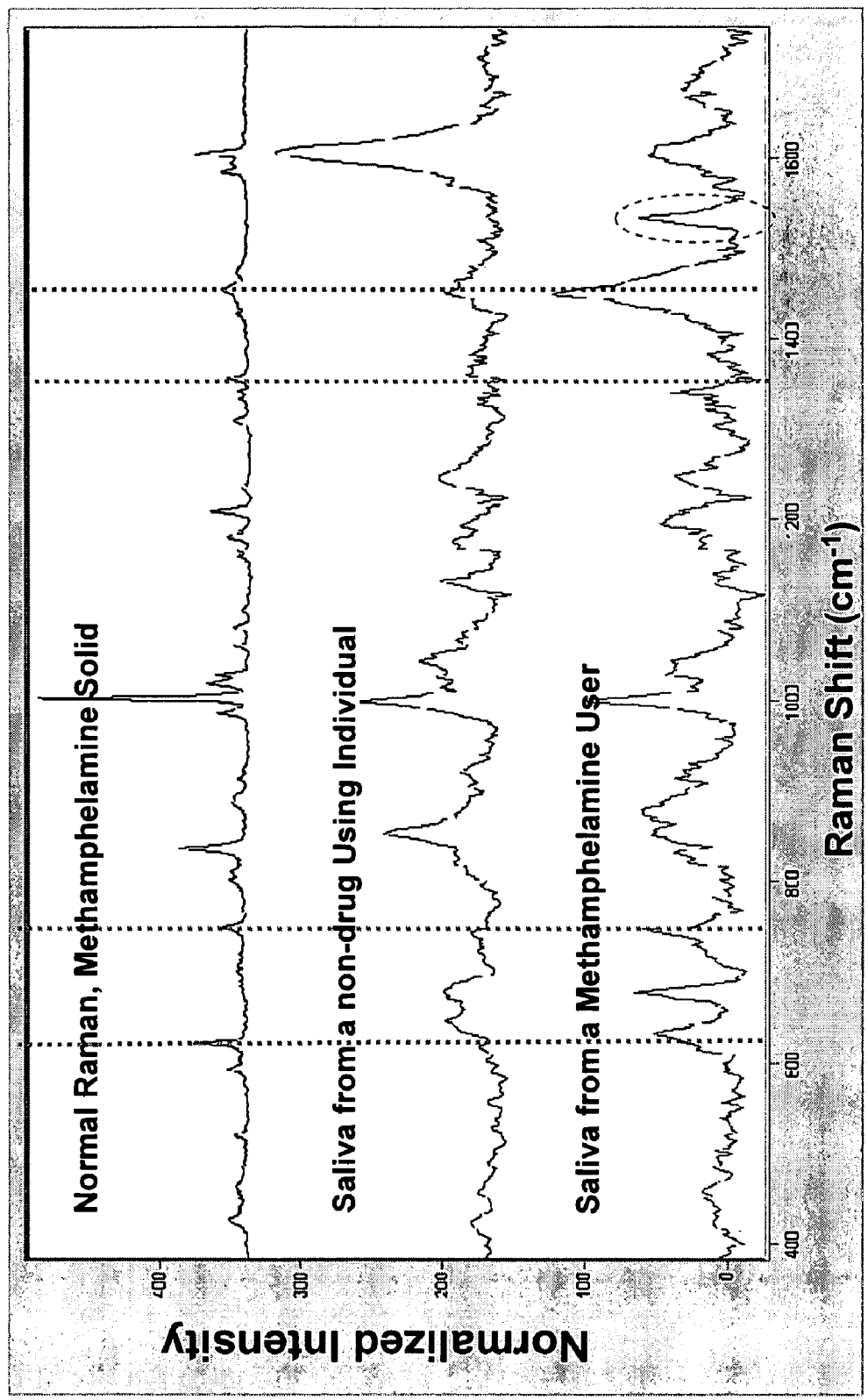
FIG. 21 illustrates an exemplified Raman spectral signature for illicit drug use detected in the saliva of an illicit drug user by the disclosed Raman scattering probe.

The disclosed systems and methods can also be used to identify illicit drug such as heroin, methamphetamine cocaine, caffeine, morphine, codeine, amphetamine, ephedrine, papaverine, narcotine, MDMA, etc. FIG. 21 shows Raman spectra from a methamphetamine solid (a type of illicit drug), a saliva sample of a non-drug using individual, and a methamphetamine drug user. The Raman spectrum from a drug-user's saliva sample shows a characteristic peak around 1030 cm$^{-1}$ and 1535 cm$^{-1}$, which can be used to indicate illicit drug use. The disclosed methods and systems can also be used to detect doping (e.g., hormone) in athletes during international sports competitions such as the Olympic Games.

Figure 22:
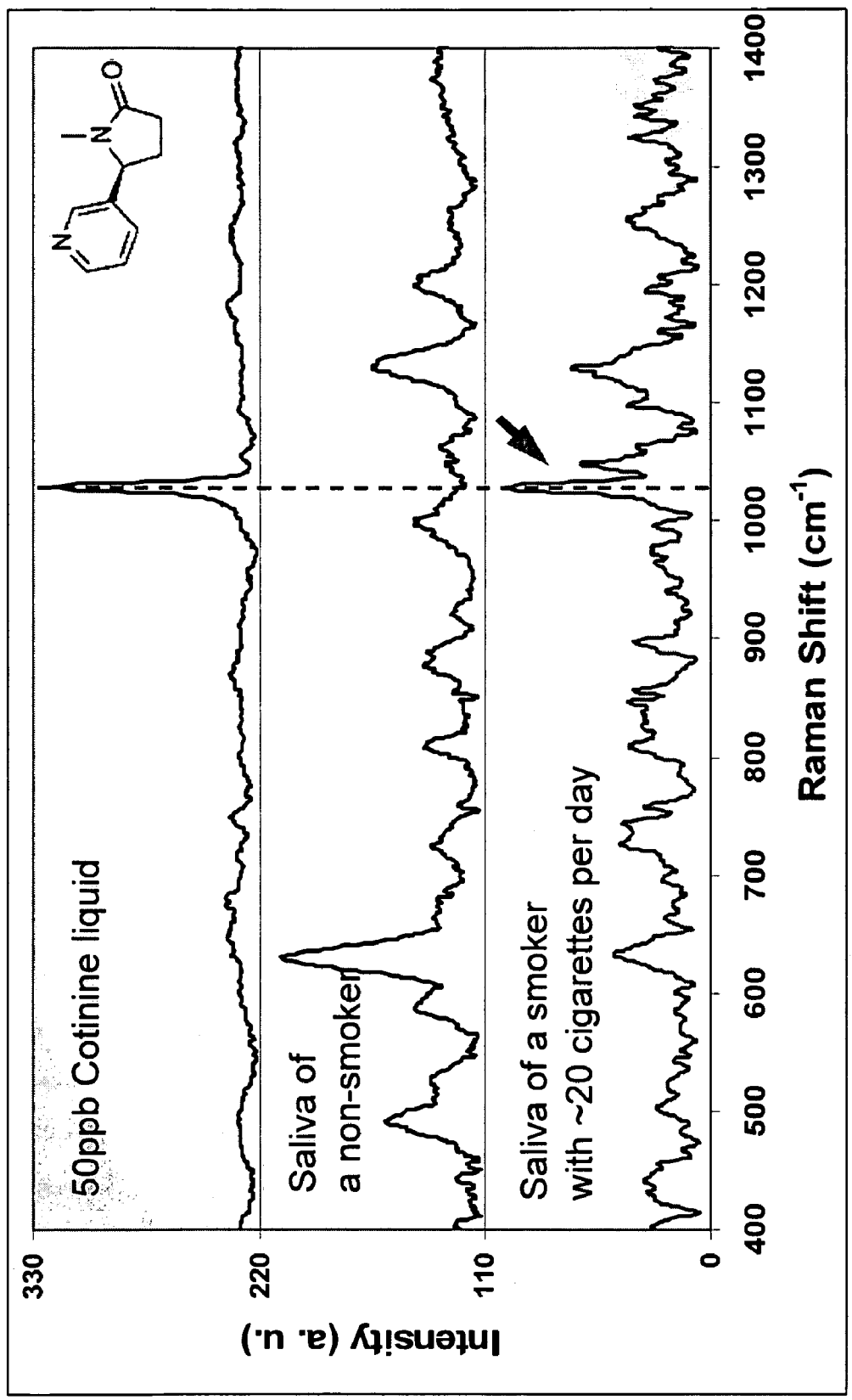
FIG. 22 illustrates an exemplified Raman spectral signature for smoking status or secondary smoking status by the disclosed Raman scattering probe.

Similarly, referring to FIG. 22, smoking status or secondary smoking status can also show spectral signature at around 1029 cm$^{-1}$ in a Raman spectrum obtained from a saliva sample of a smoker, which is absent in a non-smoking healthy individual. The signature spectral peaks around 1029 cm$^{-1}$ is associated with molecular vibration mode of cotinine which is metabolite of nicotine.

Figure 23:
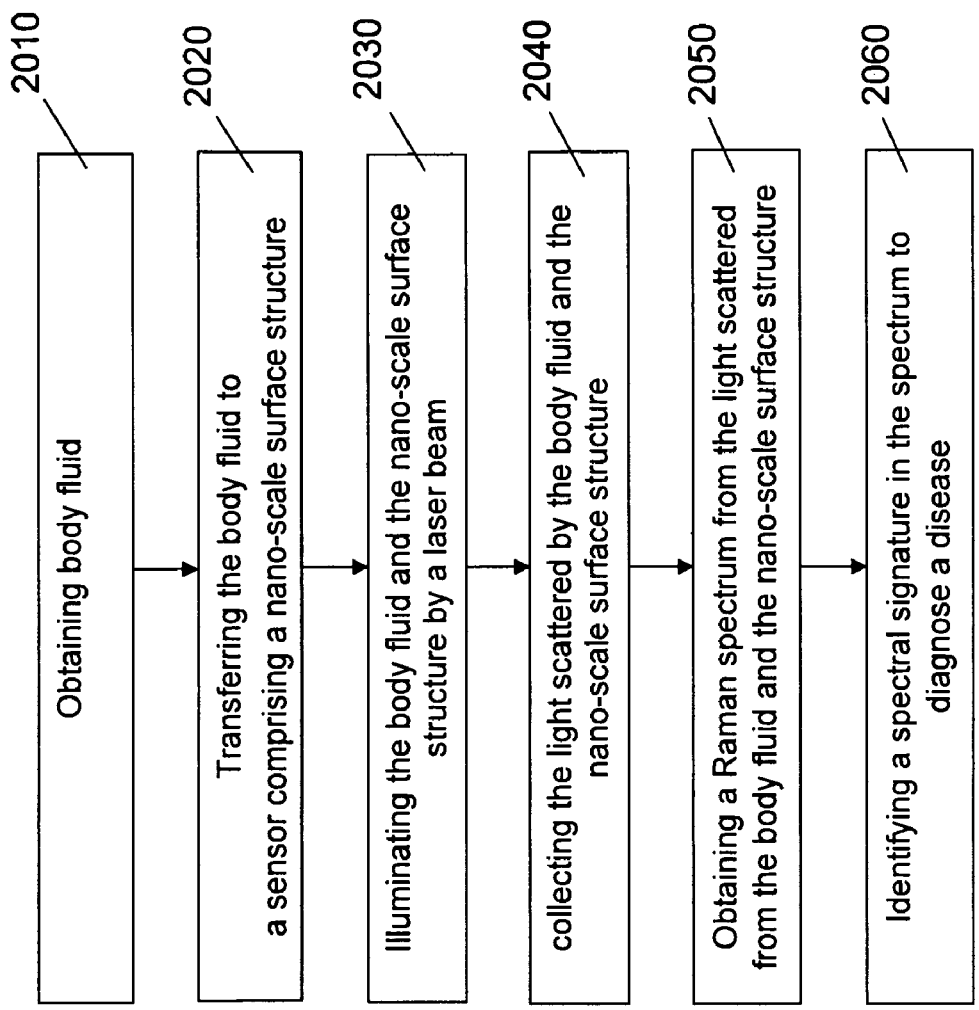
FIG. 23 is a flowchart for non-invasive disease diagnosis using the disclosed Raman scattering probe."

The non-invasive disease detection and diagnosis using the disclosed Raman scattering probe can include one of more of the following steps: referring to FIG. 23, a body fluid is first obtained from a patient or an illicit drug user (step 2010). Due to the high sensitivity of the disclosed Raman scattering sensors, the amount body fluid can be rather small. For example, the volume of the body fluid obtained from the patient can be in a range from about 100 pl to 1 ml. Examples of the body fluid can include blood, saliva, urine, serum, tear, sweat, and stomach fluid. After centrifuge, the body fluid is next transferred to a sensor (e.g., a RamanNanoChip™) comprising a nano-scale surface structure (step 2020). Molecules in the body fluid are adsorbed to the nano-scale surface structure. A laser beam is applied to illuminate the body fluid, the nano-scale surface structure, and the molecules adsorbed onto the nano-scale surface structure (step 2030). Light scattered by the body fluid, the nano-scale surface structure, and the adsorbed molecules is collected (step 2040).

A Raman spectrum is obtained from the scattered light (step 2050). One or more spectral signatures are identified in the spectrum to diagnose a disease (step 2060). Examples of the diseases that can be detected include lung cancer, breast cancer, stomach cancer, esophageal cancer, thyroid cancer, larynx cancer, liver cirrhosis, a failing kidney, ulcer cancer, ovarian cancer, uterus cancer, cervix cancer, oral cancer, leukemia, colon cancer, bladder cancer, prostate cancer, bronchus cancer, HIV, and drug addiction. As previously described, the one or more spectral signatures are at predetermined wavelengths in the Raman spectrum. The wavelengths and the characteristics of the spectral signatures are specific to the disease to be detected. For example, spectral signatures for oral and breast cancers in a saliva sample can be at around 560 cm$^{-1}$ or 1100 cm$^{1}$. A spectral signature for lung cancer in a serum sample can be at around 745 cm$^{-1}$ in the Raman spectrum. A spectral signature can include a spectral peak. The spectral signature can be identified when the spectral peak is above certain threshold. For example, a signal-to-noise ratio of the spectral peak relative to the noise background can be above 3 for the spectral signature to be positively identified.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

What is claimed is:

1. A method for non-invasive detection of a disease, comprising:
    transferring a body fluid obtained from a patient to a sensor comprising a nano-scale surface structure to allow the body fluid to come in contact with the nano-scale surface structure;
    illuminating the body fluid and the nano-scale surface structure by a laser beam;
    scattering the laser beam by the body fluid and the nano-scale surface structure to produce a scattered light;
    identifying a spectral signature around 560 $cm^{-1}$, 1100 $cm^{-1}$, or 745 $cm^{-1}$ in the Raman spectrum of the scattered light using a spectral analyzer, wherein the spectral signature comprises a spectral peak;
    calculating a signal-to-noise ratio using a peak intensity of the spectral signature and a background level in the Raman spectrum;
    determining if the signal-to-noise ratio for the spectral signature in the Raman spectrum is above a pre-determined threshold value; and
    alerting a possibility of a cancer or Human Immunodeficiency Virus (HIV) in the patient if the spectral peak is above the pre-determined threshold value.

2. The method of claim 1, wherein the body fluid includes blood, urine, serum, tear, sweat, stomach fluid, sperm, and a secrete body fluid.

3. The method of claim 1, wherein the cancer is selected from the group consisting of lung cancer, breast cancer, stomach cancer, a failing kidney, ulcer cancer, ovarian cancer, uterus cancer, cervix cancer, oral cancer, esophageal cancer, thyroid cancer, larynx cancer, colon cancer, bladder cancer, prostate cancer, and bronchus cancer.

4. The method of claim 1, wherein the body fluid includes saliva.

5. The method of claim 1, wherein the body fluid transferred to the sensor has a volume in a range from about 100 pl to 1 ml.

6. The method of claim 1, wherein the step of analyzing comprises:
    obtaining a Raman spectrum of the scattered light; and
    analyzing the Raman spectrum to detect the cancer or HIV in the patient.

7. The method of claim 1, wherein the signal-to-noise ratio is calculated using an integrated intensity in the spectral peak.

8. The method of claim 7, wherein the step of analyzing comprises:
    determining if the signal-to-noise ratio for the spectral signature in the Raman spectrum is above a pre-determined threshold value; and
    alerting a possibility of the disease in the patient if the spectral peak is above the pre-determined threshold value.

9. The method of claim 8, wherein the pre-determined threshold value for the signal-to-noise ratio is 3 or higher.

10. The method of claim 1, wherein the disease is oral cancer, wherein the body fluid is saliva, wherein the step of analyzing comprises analyzing a spectral signature around 560 $cm^{-1}$ or 1100 $cm^{-1}$ in the Raman spectrum to diagnose oral cancer in the patient.

11. The method of claim 1, wherein the disease is breast cancer, wherein the body fluid is saliva, wherein the step of analyzing comprises analyzing a spectral signature around 560 $cm^{-1}$ or 1100 $cm^{-1}$ in the Raman spectrum to diagnose breast cancer in the patient.

12. The method of claim 1, wherein the disease is lung cancer, wherein the body fluid is blood serum, wherein the step of analyzing comprises analyzing a spectral signature around 745 $cm^{-1}$ in the Raman spectrum to diagnose lung cancer in the patient.

13. The method of claim 1, wherein the disease is HIV, wherein the body fluid is saliva, wherein the step of analyzing comprises analyzing a spectral signature around 870 $cm^{-1}$ in the Raman spectrum to diagnose HIV in the patient.

14. The method of claim 1, wherein the Raman spectrum is analyzed using an algorithm including a dendrographic algorithm or a Principal Component Analysis.

15. The method of claim 1, further comprising adsorbing molecules in the body fluid by a surface of the nano-scale surface structure, wherein the step of scattering comprises scattering the laser beam by the molecules adsorbed on the surface of the nano-scale surface structure.

16. The method of claim 1, wherein the nano-scale surface structure comprises a conductive material.

17. The method of claim 16, wherein the conductive material comprises a noble metal.

18. The method of claim 1, wherein the sensor further comprises a substrate, and wherein the nano-scale surface structure comprises a plurality of columns over the substrate or a plurality of holes in the substrate.

19. The method of claim 18, wherein the sensor further comprises a conductive layer on the substrate, and wherein the plurality of columns are formed on the conductive layer.

20. The method of claim 18, wherein the sensor further comprises a conductive layer on the substrate, and wherein the plurality of holes are formed at least partially in the conductive layer.

21. The method of claim 18, wherein neighboring columns in the plurality of columns or neighboring holes in the plurality of holes are separated by a distance in the range of 10 nanometers to 1000 nanometers.

22. A method for non-invasive detection of a disease, illicit-drug use status, or smoking status, comprising:
    transferring a body fluid obtained from a patient to a sensor comprising a nano-scale surface structure to allow the body fluid to come in contact with the nano-scale surface structure, wherein the sensor includes a substrate, and a plurality of columns over the substrate or a plurality of holes in the substrate;
    illuminating the body fluid and the nano-scale surface structure by a laser beam;
    scattering the laser beam by the body fluid and the nano-scale surface structure to produce a scattered light;
    obtaining a Raman spectrum of the scattered light;
    identifying a spectral signature around a predetermined wavelength in the Raman spectrum to diagnose the disease, or to determine the illicit-drug use status or the smoking status in the patient, wherein the spectral signature includes at least one spectral peak around the predetermined wavelength in the Raman spectrum, wherein the spectral signature comprises a spectral peak;
    calculating a signal-to-noise ratio using a peak intensity of the spectral signature and the background level in the Raman spectrum;
    determining if the signal-to-noise ratio for the spectral signature in the Raman spectrum is above a pre-determined threshold value; and alerting a possibility of an illicit-drug use status or a smoking status associated with the patient if the spectral peak is above the pre-determined threshold value.

23. The method of claim 22, wherein the step of analyzing comprises:
determining if the signal-to-noise ratio for the spectral peak in the Raman spectrum is above a pre-determined threshold value; and
alerting a possibility of the disease in the patient if the spectral peak is above the pre-determined threshold value.

24. The method of claim 23, wherein the pre-determined threshold value for the signal-to-noise ratio is 3.

25. The method of claim 22, wherein the disease is oral cancer, wherein the body fluid is saliva, wherein the step of analyzing comprises analyzing a spectral signature around 560 $cm^{-1}$ or 1100 $cm^{-1}$ in the Raman spectrum to diagnose oral cancer in the patient.

26. The method of claim 22, wherein the disease is breast cancer, wherein the body fluid is saliva, wherein the step of analyzing comprises analyzing a spectral signature around 560 $cm^{-1}$ or 1100 $cm^{-1}$ in the Raman spectrum to diagnose breast cancer in the patient.

27. The method of claim 22, wherein the disease is lung cancer, wherein the body fluid is blood serum, wherein the step of analyzing comprises analyzing a spectral signature around 745 $cm^{-1}$ in the Raman spectrum to diagnose lung cancer in the patient.

28. The method of claim 22, wherein the disease is HIV, wherein the body fluid is saliva, wherein the step of analyzing comprises analyzing a spectral signature around 870 $cm^{-1}$ in the Raman spectrum to diagnose HIV in the patient.

29. The method of claim 22, wherein the body fluid is saliva, wherein the step of analyzing comprises analyzing a spectral signature around at least one of the wave numbers 1030 $cm^{-1}$ and 1535 $cm^{-1}$ in the Raman spectrum to detect status of illicit drug use by the patient.

30. The method of claim 22, wherein the body fluid is saliva, wherein the step of analyzing comprises analyzing a spectral signature around 1029 $cm^{-1}$ in the Raman spectrum to detect smoking status of the patient.

31. The method of claim 22, wherein the body fluid is saliva, wherein the step of analyzing comprises analyzing a spectral signature around 1124 $cm^{-1}$ in the Raman spectrum to diagnose diabetes in the patient.

32. The method of claim 22, wherein neighboring columns in the plurality of columns or neighboring holes in the plurality of holes are separated by a distance in the range of 10 nanometers to 1000 nanometers.

33. The method of claim 22, wherein the body fluid includes blood, saliva, urine, serum, tear, sweat, stomach fluid, sperm, and a secrete body fluid.

34. The method of claim 22, wherein the disease is selected from the group consisting of lung cancer, breast cancer, stomach cancer, liver cirrhosis, a failing kidney, ulcer cancer, ovarian cancer, uterus cancer, cervix cancer, oral cancer, leukemia, colon cancer, bladder cancer, prostate cancer, bronchus cancer, HIV(virus), diabetes, smoking status, and drug addiction.

35. The method of claim 22, wherein the disease includes an illicit use of a drug selected from a group consisting of heroin, methamphetamine, cocaine, caffeine, morphine, codeine, amphetamine, ephedrine, papaverine, narcotine, and MDMA.

36. A method for non-invasive detection of illicit-drug use status, comprising:
transferring a body fluid obtained from a patient to a sensor comprising a nano-scale surface structure to allow the body fluid to come in contact with the nano-scale surface structure;
illuminating the body fluid and the nano-scale surface structure by a laser beam;
scattering the laser beam by the body fluid and the nano-scale surface structure to produce a scattered light;
obtaining a Raman spectrum of the scattered light;
identifying a spectral signature around 1030 $cm^{-1}$ and 1535 $cm^{-1}$ in the Raman spectrum of the scattered light using a spectral analyzer, wherein the spectral signature comprises a spectral peak;
calculating a signal-to-noise ratio using a peak intensity of the spectral signature and the background level in the Raman spectrum;
determining if the signal-to-noise ratio for the spectral signature in the Raman spectrum is above a pre-determined threshold value; and
alerting a possibility of illicit-drug use status associated with the patient if the spectral peak is above the pre-determined threshold value.

* * * * *